United States Patent

Witschel et al.

(10) Patent No.: US 6,326,333 B1
(45) Date of Patent: Dec. 4, 2001

(54) PYRAZOLYLDIOXOTHIOCHROMANOYL DERIVATIVES

(75) Inventors: Matthias Witschel, Ludwigshafen; Klaus Langemann, Worms; Wolfgang von Deyn; Ulf Misslitz, both of Neustadt; Ernst Baumann, Dudenhofen; Stefan Engel, Nieder-Olm; Guido Mayer, Neustadt; Ulf Neidlein, Mannheim; Oliver Wagner; Martina Otten, both of Ludwigshafen; Karl-Otto Westphalen, Speyer; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/674,961

(22) PCT Filed: May 10, 1999

(86) PCT No.: PCT/EP99/03197

§ 371 Date: Nov. 8, 2000

§ 102(e) Date: Nov. 8, 2000

(87) PCT Pub. No.: WO99/59991

PCT Pub. Date: Nov. 25, 1999

(30) Foreign Application Priority Data

May 18, 1998 (DE) ............................................... 198 22 213

(51) Int. Cl.⁷ ....................................................... A01N 43/56
(52) U.S. Cl. ..................... 504/280; 504/282; 548/364.4
(58) Field of Search ........................ 504/282, 280; 548/364.4

(56) References Cited

U.S. PATENT DOCUMENTS 5,925,767   7/1999   Otten et al. ......................... 548/364.4

FOREIGN PATENT DOCUMENTS

| | | |
|---|---|---|
| 195 32312 | 3/1997 | (DE). |
| 2227946 | 3/1997 | (CA). |
| 629 623 | 12/1994 | (EP). |
| 712 853 | 5/1996 | (EP). |
| 728756 | 8/1996 | (EP). |
| 97/08164 | 3/1997 | (WO). |
| 97/30993 | 8/1997 | (WO). |

Primary Examiner—Amelia Owens
(74) Attorney, Agent, or Firm—Keil & Weinkauf

(57) ABSTRACT

Pyrazolyldioxothiochromanoyl derivatives of the formula I

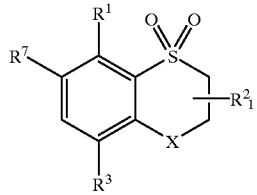

(I)

where:

X is oxygen, sulfur, S=O, S(=O)$_2$, CR$^4$R$^5$, C=O or C=NR$^6$,

R$^1$ is hydrogen, nitro, halogen, cyano, alkyl, haloalkyl, alkoxy, haloalkoxy, alkylthio, haloalkylthio, alkylsulfinyl, haloalkylsulfinyl, alkylsulfonyl, haloalkylsulfonyl, aminosulfonyl with or without substitution or sulfonylamino with or without substitution;

R$^2$ is alkyl, haloalkyl, alkoxy or haloalkoxy;

R$^3$ is hydrogen, alkyl or halogen;

R$^4$, R$^5$ are hydrogen, nitro, halogen, cyano, alkyl, haloalkyl, alkoxy, haloalkoxy, alkylthio, haloalkylthio, alkylsulfinyl, haloalkylsulfinyl, alkylsulfonyl, haloalkylsulfonyl or substituted amino; or R$^4$ and R$^5$ together form a chain which may be substituted and/or interrupted by oxygen or sulfur; or a methylidene group with or without substitution;

l is 0 to 4;

R$^7$ is substituted pyrazol-4-ylcarbonyl or substituted pyrazol-4-ylmethylidene;

and agriculturally useful salts thereof.

19 Claims, No Drawings

PYRAZOLYLDIOXOTHIOCHROMANOYL DERIVATIVES

The present invention relates to novel pyrazolyl-dioxothiochromanoyl derivatives of the formula I,

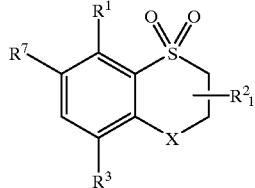

where:
- X is oxygen, sulfur, S=O, S(=O)$_2$, CR$^4$R$^5$, C=O or C=NR$^6$;
- R$^1$ is hydrogen, nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, aminosulfonyl, N—(C$_1$–C$_6$-alkyl)aminosulfonyl, N,N-di(C$_1$–C$_6$-alkyl)aminosulfonyl, N—(C$_1$–C$_6$-alkylsulfonyl)amino, N—(C$_1$–C$_6$-haloalkylsulfonyl)amino, N—(C$_1$–C$_6$-alkyl)-N—(C$_1$–C$_6$-alkylsulfonyl)amino or N—(C$_1$–C$_6$-alkyl)-N—(C$_1$–C$_6$-haloalkylsulfonyl)amino;
- R$^2$ is C$_1$–C$_6$-alkyl, C$_1$–C$_6$-haloalkyl, C$_1$–C$_6$-alkoxy or C$_1$–C$_6$-haloalkoxy;
- R$^3$ is hydrogen, C$_1$–C$_6$-alkyl or halogen;
- R$^4$,R$^5$ are hydrogen, nitro, halogen, cyano, C$_1$–C$_6$alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, N-C$_1$–C$_6$-alkylamino, N-C$_1$–C$_6$-haloalkylamino, N,N-di(C$_1$–C$_6$-alkyl)amino, N-C$_1$–C$_6$-alkoxyamino, N—(C$_1$–C$_6$-alkoxy)-N—(C$_1$–C$_6$-alkyl)amino, 1-tetrahydropyrrolyl, 1-piperidinyl, 4-morpholinyl or 1-hexahydropyrazinyl; or
- R$^4$ and R$^5$ together form an —O—(CH$_2$)$_m$—O—, —O—(CH$_2$)$_m$—S—, —S—(CH$_2$)$_m$—S— or —O—(CH$_2$)$_n$— chain which may be substituted by one to three radicals selected from the following group: halogen, cyano, C$_1$–C$_4$-alkyl, C$_1$–C$_4$-haloalkyl or C$_1$–C$_4$-alkoxycarbonyl; or
- R$^4$ and R$^5$ together form a —(CH$_2$)$_p$— chain which may be interrupted by oxygen or sulfur and/or may be substituted by one to four radicals selected from the following group: halogen, cyano, C$_1$–C$_4$-alkyl, C$_1$–C$_4$-haloalkyl or C$_1$–C$_4$-alkoxycarbonyl; or
- R$^4$ and R$^5$ together form a methylidene group which may be substituted by one or two radicals selected from the following group: halogen, cyano, hydroxyl, formyl, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl or C$_1$–C$_6$-haloalkylsulfonyl;
- R$^6$ is C$_1$–C$_6$-alkyl, C$_1$–C$_6$-haloalkyl, C$_1$–C$_6$-alkoxy or C$_1$–C$_6$-haloalkoxy;
- l is 0 to 4;
- m is 2 to 4;
- n is 1 to 5;
- p is 2 to 5;

R$^7$ is a compound IIa or IIb

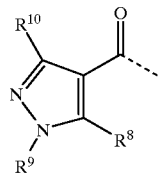

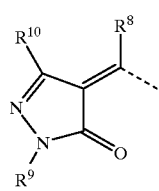

where
- R$^8$ is halogen, OR$^{11}$, SR$^{11}$, SOR$^{12}$, SO$_2$R$^{12}$, POR$^{12}$R$^{13}$, OPOR$^{12}$R$^{13}$, OPSR$^{12}$R$^{13}$, NR$^{14}$R$^{15}$, ONR$^{15}$R$^{15}$, N-bonded heterocyclyl or O—(N-bonded heterocyclyl), where the heterocyclyl radical of the two last mentioned substituents may be partially or fully halogenated and/or may carry one to three of the following radicals: nitro, cyano, C$_1$–C$_4$-alkyl, C$_1$–C$_4$-haloalkyl, C$_1$–C$_4$-alkoxy or C$_1$–C$_4$-haloalkoxy;
- R$^9$ is hydrogen, C$_1$–C$_6$alkyl, C$_1$–C$_6$-haloalkyl, hydroxyl, C$_1$–C$_6$alkoxy or C$_1$–C$_6$-haloalkoxy;
- R$^{10}$ is hydrogen, halogen, C$_1$–C$_6$alkyl, C$_1$–C$_6$-haloalkyl, hydroxyl, C$_1$–C$_6$-alkoxy, C$_1$–C$_6$-haloalkoxy, C$_1$–C$_6$-alkylthio or C$_1$–C$_6$-haloalkylthio;
- R$^{11}$ is C$_1$–C$_6$-alkyl, C$_3$–C$_6$alkenyl, C$_3$–C$_6$-haloalkenyl, C$_3$–C$_6$-alkynyl, C$_3$–C$_6$-haloalkynyl, C$_3$–C$_6$-cycloalkyl, C$_1$–C$_{20}$alkylcarbonyl, C$_2$–C$_{20}$-alkenylcarbonyl, C$_2$–C$_6$alkynylcarbonyl, C$_3$–C$_6$-cycloalkylcarbonyl, (2-norbornyl)methylcarbonyl, C$_1$–C$_6$-alkoxycarbonyl, C$_3$–C$_6$-alkenyloxycarbonyl, C$_3$–C$_6$-alkynyloxycarbonyl, C$_1$–C$_6$-alkylthiocarbonyl, C$_1$–C$_6$-alkylaminocarbonyl, C$_3$–C$_6$-alkenylaminocarbonyl, C$_3$–C$_6$-alkynylaminocarbonyl, N,N-di(C$_1$–C$_6$-alkyl)aminocarbonyl, N—(C$_3$–C$_6$-alkenyl)-N—(C$_1$–C$_6$-alkyl)aminocarbonyl, N—(C$_3$–C$_6$-alkynyl)-N—(C$_3$–C$_6$-alkyl)aminocarbonyl, N—(C$_1$–C$_6$-alkoxy)-N—(C$_1$–C$_6$-alkyl)aminocarbonyl, N—(C$_3$–C$_6$-alkenyl)-N—(C$_1$–C$_6$-alkoxy)aminocarbonyl, N—(C$_3$–C$_6$-alkynyl)-N—(C$_1$–C$_6$-alkoxy)aminocarbonyl, di(C$_1$–C$_6$-alkyl)aminothiocarbonyl, C$_1$–C$_6$-alkylcarbonyl-C$_1$–C$_6$-alkyl, C$_1$–C$_6$-alkoxyimino-C$_1$–C$_6$-alkyl, N—(C$_1$–C$_6$-alkylamino)imino-C$_1$–C$_6$-alkyl or N,N-di(C$_1$–C$_6$-alkylamino)imino-C$_1$–C$_6$alkyl, where the abovementioned alkyl, cycloalkyl and alkoxy radicals may be partially or fully halogenated and/or may carry one to three of the following groups: cyano, C$_1$–C$_4$-alkoxy, C$_1$–C$_4$-alkylthio, di(C$_1$–C$_4$-alkyl)amino, C$_1$–C$_4$-alkylcarbonyl, C$_1$–C$_4$alkoxycarbonyl, C$_1$–C$_4$-alkoxy-C$_1$–C$_4$-alkoxycarbonyl, di(C$_1$–C$_4$alkyl)amino-C$_1$–C$_4$-alkoxycarbonyl, hydroxycarbonyl, C$_1$–C$_4$-alkylaminocarbonyl, di(C$_1$–C$_4$-alkyl)aminocarbonyl, aminocarbonyl, C$_1$–C$_4$-alkylcarbonyloxy or C$_3$–C$_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxy-thiocarbonyl, heterocyclyloxycarbonyl, heterocyclyloxythiocarbonyl, phenylaminocarbonyl, N—($C_1$–$C_6$alkyl)-N-(phenyl)aminocarbonyl, heterocyclylaminocarbonyl, N—($C_1$–$C_6$-alkyl)-N-(heterocyclyl)aminocarbonyl, phenyl-$C_2$–$C_6$-alkenylcarbonyl or heterocyclyl-$C_2$–$C_6$-alkenylcarbonyl, where the phenyl and the heterocyclyl radical of the 18 lastmentioned substituents may be partially or fully halogenated and/or may carry one to three of the following radicals: nitro, cyano, $C_1$–$C_4$-alkyl, $C_1$–$C_4$-haloalkyl, $C_1C_4$-alkoxy, $C_1$–$C_4$-haloalkoxy, phenoxy, heterocyclyl or N-bonded heterocyclyl, where the three lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{12}$, $R^{13}$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, amino, $C_1$–$C_6$-alkylamino, $C_1$–$C_6$-haloalkylamino, di($C_1$–$C_6$-alkyl)amino or di($C_1$–$C_6$-haloalkyl)amino, where the abovementioned alkyl, cycloalkyl and alkoxy radicals may be partially or fully halogenated and/or may carry one to three of the following groups: cyano, $C_1$–$C_4$alkoxy, $C_1$–$C_4$-alkylthio, di($C_1$–$C_4$-alkyl)amino, $C_1$–$C_4$alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$alkoxycarbonyl, hydroxycarbonyl, $C_1$–$C_4$-alkylaminocarbonyl, di($C_1$–$C_4$-alkyl)-aminocarbonyl, aminocarbonyl, $C_1$–$C_4$-alkylcarbonyloxy or $C_3$–$C_6$-cycloalkyl;

are phenyl, heterocyclyl, phenyl-$C_1$–$C_6$-alkyl, heterocyclyl $C_1$–$C_6$-alkyl, phenoxy, heterocyclyloxy, where the phenyl and the heterocyclyl radical of the lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three radicals of the following group: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{15}$ is $C_1$–$C_6$-alkyl, $C_3$–$C_6$-alkenyl, $C_3$–$C_6$-alkynyl or $C_1$–$C_6$-alkylcarbonyl;

and agriculturally useful salts thereof.

The invention additionally relates to processes for preparing compounds of the formula I, to compositions comprising them and to the use of these derivatives or of compositions comprising them for controlling harmful plants.

Dioxothiochroman derivatives which are linked to a substituted (5-hydroxypyrazol-4-yl)carbonyl radical are known from the literature, for example from DE-A 19 532 312, WO 97/30993 and WO 97/08164. However, the herbicidal properties of the prior art compounds and their compatibility with crop plants are not entirely satisfactory.

It is an object of the present invention to provide novel biologically, in particular herbicidally, active compounds having improved properties.

We have found that this object is achieved by the pyrazolyl-dioxothiochromanoyl derivatives of the formula I and their herbicidal action.

Furthermore, the invention provides herbicidal compositions comprising the compounds I and having very good herbicidal activity. Additionally, the invention provides processes for preparing these compositions and methods for controlling undesirable plant growth using the compounds I.

Depending on the substitution pattern, the compounds of the formula I may contain one or more chiral centers and, if this is the case, be present as enantiomers or mixtures of diastereomers. The invention provides both pure enantiomers or diastereomers and mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium where, if desired, one to four hydrogen atoms may be replaced by $C_1$–$C_4$alkyl, hydroxy-$C_1$–$C_4$ alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)-eth-1-ylammonium, di(2-hydroxyeth-1-yl)ammonium, trimethylbenzylammonium, and furthermore phosphonium ions, sulfonium ions, preferably tri($C_1$–$C_4$-alkyl)sulfonium and sulfoxonium ions, preferably tri ($C_1$–$C_4$alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and also the anions of $C_1$–$C_4$-alkanoic acids, preferably formate, acetate, propionate and butyrate.

The organic molecular moieties mentioned for the substituents $R^1$–$R^{15}$ or as radicals on phenyl and heterocyclyl radicals represent collective terms for individual listings of the individual group members. All hydrocarbon chains, i.e. all alkyl, haloalkyl, alkoxy, haloalkoxy, alkylthio, haloalkylthio, alkyl-sulfinyl, haloalkylsulfinyl, alkylsulfonyl, haloalkylsulfonyl, N-alkylaminosulfonyl, N,N-dialkylaminosulfonyl, N-alkylamino, N,N-dialkylamino, N-haloalkylamino, N,N-dihaloalkylamino, N-alkoxyamino, N-alkoxy-N-alkylamino, N-alkylcarbonylamino, N-alkylsulfonylamino, N-haloalkylsulfonylamino, N-alkyl-N-alkyl-sulfonylamino, N-alkyl-N-haloalkylsulfonylamino, alkylcarbonyl, alkoxycarbonyl, alkylthiocarbonyl, alkylcarbonyloxy, alkylaminocarbonyl, dialkylaminocarbonyl, dialkylaminothiocarbonyl, alkoxyalkyl, alkylcarbonylalkyl, alkoxyiminoalkyl, N-(alkylamino)iminoalkyl, N-(dialkylamino)iminoalkyl, phenylalkenylcarbonyl, heterocyclylalkenylcarbonyl, N-alkoxy-N-alkyl aminocarbonyl, N-alkyl-N-phenylaminocarbonyl, N-alkyl-N-heterocyclylaminocarbonyl, phenylalkyl, heterocyclylalkyl, phenyl-carbonylalkyl, heterocyclylcarbonylalkyl, dialkylaminoalkoxy-carbonyl, alkoxyalkoxycarbonyl, alkenylcarbonyl, alkenyloxy-carbonyl, alkenylaminocarbonyl, N-alkenyl-N-alkylaminocarbonyl, N-alkenyl-N-alkoxyaminocarbonyl, alkynylcarbonyl, alkynyloxy-carbonyl, alkynylaminocarbonyl, N-alkynyl-N-alkylaminocarbonyl, N-alkynyl-Nalkoxyaminocarbonyl, alkenyl, alkynyl, haloalkenyl, haloalkynyl, alkenyloxy and alkynyloxy moieties may be straight-chain or branched. Unless stated otherwise, halogenated substituents preferably carry one to five identical or different halogen atoms. Halogen is in each case fluorine, chlorine, bromine or iodine.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkylcarbonyl-$C_1$–$C_6$-alkyl, $C_1$–$C_6$-alkoxyimino-$C_1$–$C_6$-alkyl, N—($C_1$–$C_6$-alkylamino)imino-$C_1$–$C_6$-alkyl, N-(di-$C_1$–$C_6$-alkylamino)iminol-$C_1$–$C_6$alkyl, N—($C_1$–$C_6$-alkoxy)-N—($C_1$–$C_6$-alkyl)aminocarbonyl, N—($C_{36}$-alkenyl)-N—($C_1$–$C_6$-alkyl)aminocarbonyl, ($C_3$–$C_6$-alkynyl)-N—($C_1$–$C_6$-alkyl)aminocarbonyl, N—($C_1$–$C_6$-alkyl)-N-phenylaminocarbonyl, N—($C_1$–$C_6$-alkyl)-N-heterocyclylaminocarbonyl, phenyl-$C_1$–$C_6$alkyl, N—($C_1$–$C_6$-alkyl)-N—($C_1$–$C_6$-alkylsulfonyl)amino, N—($C_1$–$C_6$alkyl)-N—($C_1C_6$-haloalkylsulfonyl)amino, heterocyclyl-$C_1$–$C_6$-alkyl, phenylcarbonyl-$C_1$–$C_6$-alkyl, hetero-cyclylcarbonyl-$C_1$–$C_6$-alkyl: $C_1$–$C_4$-alkyl, as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of N—$C_1$–$C_6$-haloalkylamino and N,N-(di-$C_1$–$C_6$-haloalkyl)amino: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chloro-hexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of N—$C_1$–$C_6$-alkoxyamino, N—$C_1$–$C_6$-alkoxy-N—$C_1$–$C_6$-alkylamino, $C_1$–$C_6$-alkoxyimino-$C_1$–$C_6$-alkyl, —N—($C_1$–$C_6$alkoxy)-N—($C_1$–$C_6$-alkyl)aminocarbonyl, N—($C_3$–$C_6$-alkenyl)-N—($C_1$–$C_6$-alkoxy)aminocarbonyl and N—($C_3$–$C_6$-alkynyl)-N—($C_1$–$C_6$-alkoxy)aminocarbonyl: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-tri-methylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e. for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio or 1,1-dimethylethylthio;

$C_1$–$C_6$-alkylthio and the alkylthio moieties of $C_1$–$C_6$-alkylthiocarbonyl: $C_1$–$C_4$-alkylthio as mentioned above, and also, for example pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_6$-haloalkylthio: a $C_1$–$C_4$-alkylthio radical as mentioned above which is partially or fully substituted by fluorine, chlorine, bromine and/or iodine, i.e. for example fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, nonafluorobutylthio, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: a $C_1$–$C_6$-alkylsulfinyl radical as mentioned above which is partially or fully substituted by fluorine, chlorine, bromine and/or iodine, i.e. for example fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_6$-alkylsulfonyl ($C_1$–$C_6$-alkyl-S(=O)$_2$—), and the alkylsulfonyl radicals of N—($C_1$–$C_6$-alkylsulfonyl) amino and N—($C_1$–$C_6$-alkyl)-N—($C_1$–$C_6$-alkylsulfonyl)amino: for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl, and the haloalkylsulfonyl radicals of N—($C_1$–$C_6$-haloalkylsulfonyl)amino and N—($C_1$–$C_6$-alkyl)-N—($C_1$–$C_6$-haloalkylsulfonyl) amino: a $C_1$–$C_6$-alkylsulfonyl radical as mentioned above which is partially or fully substituted by fluorine, chlorine, bromine and/or iodine, i.e. for example fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino, and the alkylamino radicals of N—($C_1$–$C_6$-alkoxy)-N—($C_1$–$C_6$-alkyl)amino and N—($C_1$–$C_6$-alkylamino)imino-$C_1$–$C_6$alkyl, i.e. for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

($C_1$–$C_4$-alkylamino)sulfonyl: for example methylaminosulfonyl, ethylaminosulfonyl, propylaminosulfonyl, 1-methylethylaminosulfonyl, butylaminosulfonyl, 1-methylpropylaminosulfonyl, 2-methylpropylaminosulfonyl or 1,1-dimethylethylaminosulfonyl;

($C_1C_6$-alkylamino)sulfonyl: ($C_1$–$C_4$-alkylamino)sulfonyl as mentioned above, and also, for example, pentylaminosulfonyl, 1-methylbutylaminosulfonyl, 2-methylbutylaminosulfonyl, 3-methylbutylaminosulfonyl, 2,2-dimethylpropylaminosulfonyl, 1-ethylpropylaminosulfonyl, hexylaminosulfonyl, 1,1-dimethylpropylaminosulfonyl, 1,2-dimethylpropylaminosulfonyl, 1-methylpentylaminosulfonyl, 2-methylpentylaminosulfonyl, 3-methylpentylaminosulfonyl, 4-methylpentylaminosulfonyl, 1,1-dimethylbutylaminosulfonyl, 1,2-dimethylbutylaminosulfonyl, 1,3-dimethylbutylaminosulfonyl, 2,2-dimethylbutylaminosulfonyl, 2,3-dimethylbutylaminosulfonyl, 3,3-dimethylbutylaminosulfonyl, 1-ethylbutylaminosulfonyl, 2-ethylbutylaminosulfonyl, 1,1,2-trimethylpropylaminosulfonyl, 1,2,2-trimethylpropylaminosulfonyl, 1-ethyl-1-methylpropylaminosulfonyl or 1-ethyl-2-methylpropylaminosulfonyl;

di-($C_1$–$C_4$-alkyl)aminosulfonyl: for example N,N-dimethylaminosulfonyl, N,N-diethylaminosulfonyl, N,N-di(1-methylethyl)aminosulfonyl, N,N-dipropylaminosulfonyl, N,N-dibutylaminosulfonyl, N,N-di(1-methylpropyl)aminosulfonyl, N,N-di-(2-methylpropyl)aminosulfonyl, N,N-di(1,1-dimethylethyl)aminosulfonyl, N-ethyl-N-methylaminosulfonyl, N-methyl-N-propylaminosulfonyl, N-methyl-N-(1-methylethyl)aminosulfonyl, N-butyl-N-methylaminosulfonyl, N-methyl-N-(1-methylpropyl)aminosulfonyl, N-methyl-N-(2-methylpropyl)aminosulfonyl, N-(1,1-dimethylethyl)-N-methylaminosulfonyl, N-ethyl-N-propylaminosulfonyl, N-ethyl-N-(1-methylethyl)aminosulfonyl, N-butyl-N-ethylaminosulfonyl, N-ethyl-N-(1-methylpropyl)aminosulfonyl, N-ethyl-N-(2-methylpropyl)aminosulfonyl, N-ethyl-N-(1,1-dimethylethyl)aminosulfonyl, N-(1-methylethyl)-N-propylaminosulfonyl, N-butyl-N-propylaminosulfonyl, N-(1-methylpropyl)-N-propylaminosulfonyl, N-(2-methylpropyl)-N-propylaminosulfonyl, N-(1,1-dimethylethyl)-N-propylaminosulfonyl, N-butyl-N-(1-methylethyl)aminosulfonyl, N-(1-methylethyl)-N-(1-methylpropyl)aminosulfonyl, N-(1-methylethyl)-N-(2-methylpropyl)aminosulfonyl, N-(1,1-dimethylethyl)-N-(1-methylethyl)aminosulfonyl, N-butyl-N-(1-methylpropyl)aminosulfonyl, N-butyl-N-(2-methylpropyl)aminosulfonyl, N-butyl-N-(1,1-dimethylethyl)aminosulfonyl, N-(1-methylpropyl)-N-(2-methylpropyl)aminosulfonyl, N-(1,1-dimethylethyl)-N-(1-methylpropyl)aminosulfonyl or N-(1,1-dimethylethyl)-N-(2-methylpropyl)aminosulfonyl;

di-($C_1$–$C_6$alkyl)aminosulfonyl: di-($C_1C_4$-alkyl)aminosulfonyl as mentioned above, and also, for example, N-methyl-N-pentylaminosulfonyl, N-methyl-N-(1-methylbutyl)aminosulfonyl, N-methyl-N-(2-methylbutyl)aminosulfonyl, N-methyl-N-(3-methylbutyl)aminosulfonyl, N-methy-N-(2,2-dimethylpropyl)aminosulfonyl, N-methyl-N-(1-ethylpropyl)aminosulfonyl, N-methyl-N-hexylaminosulfonyl, N-methyl-N-(1,1-dimethylpropyl)aminosulfonyl, N-methyl-N-(1,2-dimethylpropyl)aminosulfonyl, N-methyl-N-(1-methylpentyl)aminosulfonyl, N-methyl-N-(2-methylpentyl)aminosulfonyl, N-methyl-N-(3-methylpentyl)aminosulfonyl, N-methyl-N-(4-methylpentyl)aminosulfonyl, N-methyl-N-(1,1-dimethylbutyl)aminosulfonyl, N-methyl-N-(1,2-dimethylbutyl)aminosulfonyl, N-methyl-N-(1,3-dimethylbutyl)aminosulfonyl, N-methyl-N-(2,2-dimethylbutyl)aminosulfonyl, N-methyl-N-(2,3-dimethylbutyl)aminosulfonyl, N-methyl-N-(3,3-dimethylbutyl)aminosulfonyl, N-methyl-N-(1-ethylbutyl)aminosulfonyl, N-methyl-N-(2-ethylbutyl)aminosulfonyl, N-methyl-N-(1,1,2-trimethylpropyl)aminosulfonyl, N-methyl-N-(1,2,2-trimethylpropyl)aminosulfonyl, N-methyl-N-(1-ethyl-1-methylpropyl)aminosulfonyl, N-methyl-N-(1-ethyl-2-methylpropyl)aminosulfonyl, N-ethyl-N-pentylaminosulfonyl, N-ethyl-N-(1-methylbutyl)aminosulfonyl, N-ethyl-N-(2-methylbutyl)aminosulfonyl, N-ethyl-N-(3-methylbutyl)aminosulfonyl, N-ethyl-N-(2,2-dimethylpropyl)aminosulfonyl, N-ethyl-N-(1-ethylpropyl)aminosulfonyl, N-ethyl-N-hexylaminosulfonyl, N-ethyl-N-(1,1-dimethylpropyl)aminosulfonyl, N-ethyl(1,2-dimethylpropyl)aminosulfonyl, N-ethyl-N-(1-methylpentyl)aminosulfonyl, N-ethyl-N-(2-methylpentyl)aminosulfonyl, N-ethyl-N-(3-methylpentyl)aminosulfonyl, N-ethyl-N-(4-methylpentyl)aminosulfonyl, N-ethyl-N-(1,1-dimethylbutyl)aminosulfonyl, N-ethyl-N-(1,2-dimethylbutyl)aminosulfonyl, N-ethyl-N-(1,3-dimethylbutyl)aminosulfonyl, N-ethyl-N-(2,2-dimethylbutyl)aminosulfonyl, N-ethyl(2,3-dimethylbutyl)aminosulfonyl, N-ethyl-N-(3,3-dimethylbutyl)aminosulfonyl, N-ethyl (1-ethylbutyl)aminosulfonyl, N-ethyl-N-(2-ethylbutyl)aminosulfonyl, N-ethyl-N-(1,1,2-trimethylpropyl)aminosulfonyl, N-ethyl-N-(1,2,2- trimethylpropyl)aminosulfonyl, N-ethyl-N-(1-ethyl-1-methylpropyl)aminosulfonyl, N-ethyl-N-(1-ethyl-2-methylpropyl)aminosulfonyl, N-propyl-N-pentylaminosulfonyl, N-butyl-N-pentylaminosulfonyl, N,N-dipentylaminosulfonyl, N-propyl-N-hexylaminosulfonyl, N-butyl-N-hexylaminosulfonyl, N-pentyl-N-hexylaminosulfonyl or N,N-dihexylaminosulfonyl;

di-($C_1$–$C_4$-alkyl)amino, and the dialkylamino radicals of di($C_1$–$C_4$-alkyl)amino-$C_1$–$C_4$-alkoxycarbonyl and N-(di-$C_1$–$C_4$-alkylamino)imino-$C_1$–$C_6$-alkyl, i.e. for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-ethylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,-dimethylethyl)-N-(1-methylpropyl)amino or N-(1,1-dimethylethyl)-N-(2-methylpropyl)amino;

di-($C_1$–$C_6$-alkyl)amino, and the dialkylamino radicals of di($C_1$–$C_6$-alkyl)aminoimino-$C_1$–$C_6$-alkyl: di-($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonylamino, $C_1$–$C_6$-alkylcarbonyl-$C_1$–$C_6$-alkyl: $C_1$–$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_{20}$-alkylcarbonyl: $C_1$–$C_6$-alkylcarbonyl as mentioned above, and also heptylcarbonyl, octylcarbonyl, pentadecylcarbonyl or heptadecylcarbonyl;

$C_1$–$C_4$-alkoxycarbonyl, and the alkoxycarbonyl moieties of di($C_1$–$C_4$-alkyl)amino-$C_1$–$C_4$-alkoxycarbonyl: i.e. for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

($C_1$–$C_6$-alkoxy)carbonyl: ($C_1$–$C_4$-alkoxy)carbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, Hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di-($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

di-($C_1$–$C_6$-alkyl)aminocarbonyl: di-($C_1$–$C_4$-alkyl)aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl)aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di-($C_1$–$C_6$-alkyl)aminothiocarbonyl: for example N,N-dimethylaminothiocarbonyl, N,N-diethylaminothiocarbonyl, N,N-di(1-methylethyl)aminothiocarbonyl, N,N-dipropylaminothiocarbonyl, N,N-dibutylaminothiocarbonyl, N,N-di(1-methylpropyl)aminothiocarbonyl, N,N-di(2-methylpropyl)aminothiocarbonyl, N,N-di(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl)aminothiocarbonyl, N-ethyl-N-(2-methylpropyl)aminothiocarbonyl, N-ethyl-N-(1,1-dimethylethyl)aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl)aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2-methylpentyl)aminothiocarbonyl, N-methyl-N-(3- methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)aminothiocarbonyl, N-ethyl-N-(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_4$-alkoxy-$C_1$–$C_4$-alkyl: $C_1$–$C_4$-alkyl which is substituted by $C_1$–$C_4$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

$C_1$–$C_4$-alkoxy-$C_1$–$C_4$-alkoxy, and the alkoxyalkoxy moieties of $C_1$–$C_4$-alkoxy-$C_1$–$C_4$-alkoxycarbonyl: $C_1$–$C_4$-alkoxy which is substituted by $C_1$–$C_4$-alkoxy as mentioned above, i.e., for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl, $C_3$–$C_6$-alkenylaminocarbonyl, N-($C_3$–$C_6$-alkenyl)-N-($C_1$–$C_6$-alkyl)aminocarbonyl, N-($C_3$–$C_6$-alkenyl)-N-($C_1$–$C_6$-alkoxy)aminocarbonyl: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-methylbut-2-en-1-yl, 1,3-dimethylbut-3-en-1-yl, 2,2-dimethylbut-3-en-1-yl, 2,3-dimethylbut-2-en-1-yl, 2,3-dimethylbut-3en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and also ethenyl;

$C_2$–$C_{20}$-alkenyl as alkenyl radical of $C_2$–$C_{20}$-alkenylcarbonyl: $C_{2-6}$-alkenyl, as mentioned above, and also hept-6-en-1-yl, oct-7-en-1-yl, non-8-en-1-yl, dec-9-en-1-yl, dodec-11-en-1-yl, hexadec-15-en-1-yl or octadec-17-en-1-yl;

$C_3$–$C_6$-haloalkenyl: a $C_{3-6}$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N-($C_3$–$C_6$-alkynyl)-N-($C_1$–$C_6$-alkyl)aminocarbonyl, N-($C_3$–$C_6$-alkynyl)-N-($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e., for example, 1,1-difluoroprop-2-yn-1-yl, 3-iodoprop-2-yn-1-yl, 4-fluoro-but- 2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

heterocyclyl, and the heterocyclyl moieties of heterocyclyloxy, heterocyclylcarbonyl, heterocyclyl-$C_1$–$C_6$-alkyl, heterocyclyloxycarbonyl, heterocyclyloxythiocarbonyl, heterocyclyl-$C_2$–$C_6$-alkenylcarbonyl, heterocyclylcarbonyl-$C_1$–$C_6$-alkyl, N-($C_1$–$C_6$-alkyl)-N-(heterocyclyl)aminocarbonyl, heterocyclylaminocarbonyl: a saturated, partially saturated or unsaturated 5- or 6-membered heterocyclic ring which is attached via carbon and contains one to four identical or different heteroatoms selected from the following group: oxygen, sulfur or nitrogen, i.e., for example, 5-membered rings having one heteroatom such as: tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl or pyrrol-3-yl;

5-membered rings having two heteroatoms such as: tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5ihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl or thiazol-5-yl;

5-membered rings having three heteroatoms such as: 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$oxadiazolin-5-yl, 1,2,4-$\Delta^2$-oxadiazolin-3-yl, 1,2,4-$\Delta^2$oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^{4+}$thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$- triazolin-5-yl, 1,2,4-Δ²-triazolin-3-yl, 1,2,4-Δ²-triazolin-5-yl, 1,2,4-Δ³-triazolin-3-yl, 1,2,4-Δ³-triazolin-5-yl, 1,2,4-Δ¹-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxa-diazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl or 1,2,4-triazol-3-yl;

5-membered rings having four heteroatoms such as: tetrazol-5-yl, 6-membered rings having one heteroatom such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl or pyridin-4-yl;

6-membered ring having two heteroatoms such as 1,3-dioxan-2-yl, 1,3-dioxan4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1, 2-thiazin6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl, pyridazin-3-yl, pyridazin-4-yl, pyrimidin-2-yl, pyrimidin-4-yl, pyrimidin-5-yl or pyrazin-2-yl;

6-membered ring having three heteroatoms such as: 1,3,5-triazin-2-yl, 1,2,4-triazin-3-yl, 1,2,4-triazin-5-yl or 1,2,4-triazin-6-yl;

6-membered ring having four heteroatoms such as: 1,2,4,5-tetrazin-3-yl;

where, if appropriate, the sulfur of the abovementioned heterocycles may be oxidized to S=O or $S(=O)_2$ and where a bicyclic ring system may be formed with a fused-on phenyl ring or with a $C_3$–$C_6$-carbocycle or with a further 5- or 6-membered heterocycle.

N-bonded heterocyclyl and the N-bonded heterocyclyl moieties of O-(N-bonded heterocyclyl): a saturated, partially saturated or unsaturated 5- or 6-membered N-bonded heterocyclic ring which contains at least one nitrogen and, if appropriate, one to three identical or different heteroatoms selected from the following group: oxygen, sulfur or nitrogen, i.e., for example, N-bonded 5-membered rings such as: tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl, tetrazol-1-yl;

and also N-bonded 6-membered rings such as: piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazinoxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

and also N-bonded cyclic imides such as:

phthalimide, tetrahydrophthalimide, succinimide, maleimide, glutarimide, 5-oxotriazolin-1-yl, 5-oxo-1,3,4-oxadiazolin-4-yl or 2,4-dioxo-(1H,3H)-pyrimidin-3-yl;

where a bicyclic ring system may be formed with a fused-on phenyl ring or with a $C_3$–$C_6$-carbocycle or a further 5- or 6-membered heterocycle.

All phenyl rings or heterocyclyl radicals and also all phenyl components in phenoxy, phenyl-$C_1$–$C_6$-alkyl, phenylcarbonyl-$C_1$–$C_6$-alkyl, phenylcarbonyl, phenylalkenylcarbonyl, phenoxycarbonyl, phenyloxythiocarbonyl, phenylaminocarbonyl and N-($C_1$–$C_6$-alkyl)-N-phenylaminocarbonyl or heterocyclyl components in heterocyclyloxy, heterocyclyl-$C_1$–$C_6$-alkyl, heterocyclylcarbonyl-$C_1$–$C_6$-alkyl, heterocyclylcarbonyl, heterocyclyloxythiocarbonyl, heterocyclylalkenylcarbonyl, heterocyclyloxycarbonyl, heterocyclylaminocarbonyl and N-($C_1$–$C_6$-alkyl)-N-heterocyclylaminocarbonyl, are, unless stated otherwise, preferably unsubstituted or carry one to three halogen atoms and/or a nitro group, a cyano radical and/or one or two methyl, trifluoromethyl, methoxy or trifluoromethoxy substituents.

The compounds of the formula I according to the invention where $R^7$=IIa are designated as compounds of the formula Ia, and the compounds of the formula I where $R^7$=IIb are designated as Ib.

Particular importance is given to the compounds of the formula I according to the invention, where $R^{11}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_{20}$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl, N-($C_3$–$C_6$-alkynyl)-N-($C_1$–$C_6$-alkoxy)aminocarbonyl, di-($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_6$-alkyl, N-($C_1$–$C_6$-alkylamino)imino-$C_1$–$C_6$-alkyl or N,N-di-($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenylaminocarbonyl, N-($C_1$–$C_6$-alkyl)-N-(phenyl)-aminocarbonyl, heterocyclylaminocarbonyl, N-($C_1$–$C_6$-alkyl)-N-(heterocyclyl)aminocarbonyl, phenyl-$C_2$–$C_6$-alkenylcarbonyl or heterocyclyl-$C_2$–$C_6$-alkenylcarbonyl, where the phenyl and the heterocyclyl radical of the 18 lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy, Heterocyclyl or N-bonded heterocyclyl, where the two lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

With respect to the use of the compounds of the formula I according to the invention as herbicides, the variables preferably have the meanings below, in each case on their own or in combination:

X is S(=O)$_2$, $CR^4R^5$, C=O or C=N—$R^6$;

$R^1$ is nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl or $C_1$–$C_6$-haloalkylsulfonyl;

$R^3$ is hydrogen;

$R^4$,$R^5$ are hydrogen, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl or $C_1$–$C_6$-haloalkylsulfonyl; or $R^4$ and $R^5$ together form an —O—(CH$_2$)$_m$—O—, —O—(CH$_2$)$_m$—S—, —S—(CH$_2$)$_m$—S— or —O—(CH$_2$)$_n$— chain which may be substituted by one to three radicals selected from the following group: halogen, cyano, $C_1$–$C_4$-alkyl, $C_1$–$C_4$-haloalkyl or $C_1$–$C_4$-alkoxycarbonyl; or $R^4$ and $R^5$ together form a —(CH$_2$)$_p$— chain which may be interrupted by oxygen or sulfur and/or may carry one to four radicals selected from the following group: halogen, cyano, $C_1$–$C_4$-alkyl, $C_1$–$C_4$-haloalkyl or $C_1$–$C_4$-alkoxycarbonyl; or $R^4$ and $R^5$ together form a methylidene group which may be substituted by one to two radicals selected from the following group: halogen, cyano, $C_1$–$C_6$-alkyl, $C_1$–$C_6$-haloalkyl, $C_1$–$C_6$-alkoxy or $C_1$–$C_6$-haloalkoxy;

$R^6$ is $C_1$–$C_6$-alkoxy or $C_1$–$C_6$-haloalkoxy;

l is 0;

m is 2 to 4;

n is 1 to 5;

p is 2 to 5;

$R^7$ is a compound IIa or IIb

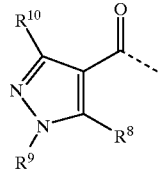

IIa

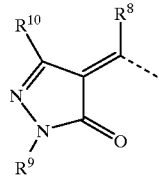

IIb where
$R^8$ is halogen, $OR^{11}$, $SR^{11}$, $SO_2R^{12}$, $POR^{12}R^{13}$, $OPOR^{12}R^{13}$, $OPSR^{12}R^{13}$, $NR^{14}R^{15}$, $ONR^{15}R^{15}$, N-bonded heterocyclyl or O-(N-bonded heterocyclyl), where the heterocyclyl radical of the two lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^9$ is hydrogen, $C_1$–$C_6$-alkyl or $C_1$–$C_6$-haloalkyl;
$R^{10}$ is hydrogen, $C_1$–$C_6$-alkyl or $C_1$–$C_6$-haloalkyl;
$R^{11}$ is $C_1$–$C_6$-alkyl, $C_3$–$C_6$-alkenyl, $C_3$–$C_6$-haloalkenyl, $C_3$–$C_6$-alkynyl, $C_1$–$C_{20}$-alkylcarbonyl, $C_2$–$C_{20}$-alkenylcarbonyl, $C_3$–$C_6$-cycloalkylcarbonyl, (2-norbornyl)methylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl, N-($C_3$–$C_6$-alkynyl)-N-($C_1$–$C_6$-alkoxy)aminocarbonyl, di-($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_{16}$-alkyl, N-($C_1$–$C_6$-alkylamino)imino-$C_1$–$C_6$-alkyl or N,N-di-($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenyl-$C_2$–$C_6$-alkenylcarbonyl or heterocyclyl-$C_2$–$C_6$-alkenylcarbonyl, where the phenyl and the heterocyclyl radical of the 14 lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy, phenoxy, heterocyclyl or N-bonded heterocyclyl, where the three lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{12}$, $R^{13}$ are $C_1$–$C_6$-alkyl, $C_3$–$C_6$-alkenyl, $C_3$–$C_6$-haloalkenyl, $C_3$–$C_6$-cycloalkyl, hydroxyl, $C_1$–$C_6$-alkoxy or di-($C_1$–$C_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

are phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di-($C_1$–$C_6$-alkyl)amino, where the abovementioned alkyl, cycloalkyl and alkoxy radicals may be partially or fully halogenated and/or may carry one to three radicals of the following group:

cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{15}$ is $C_1$–$C_6$-alkyl or $C_3$–$C_6$-alkenyl.

In this case particular importance is given to the compounds of the formula I according to the invention, where $R^{11}$ is $C_1$–$C_6$-alkyl, $C_3$–$C_6$-alkenyl, $C_3$–$C_6$-haloalkenyl, $C_3$–$C_6$-alkynyl, $C_1$–$C_{20}$-alkylcarbonyl, $C_2$–$C_6$-alkenylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di-($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl, N-($C_3$–$C_6$-alkynyl)-N-($C_1$–$C_6$-alkoxy)aminocarbonyl-$C_1$–$C_6$-alkoxyimino-$C_1$–$C_6$-alkyl, di-($C_1$–$C_6$-alkyl)aminothiocarbonyl, $C_1$–$C_6$-alkylcarbonyl-$C_1$–$C_6$-alkyl, N-($C_1$–$C_6$-alkylamino)imino-$C_1$–$C_6$-alkyl or N,N-di-($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenyl-$C_2$–$C_6$-alkenylcarbonyl or heterocyclyl-$C_2$–$C_6$-alkenylcarbonyl, where the phenyl and the heterocyclyl radical of the 14 lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy, phenoxy, heterocyclyl or N-bonded heterocyclyl, where the three lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

Particular preference is given to compounds of the formula I, where the variables have the following meanings, in each case on their own or in combination:

X is $S(=O)_2$ or $CR^4R^5$, $R^1$ is halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl; in particular halogen such as chlorine or bromine, $C_1$–$C_6$-alkyl such as methyl or ethyl or $C_1$–$C_6$-alkoxy such as methoxy or ethoxy; particularly preferably chlorine, methyl or methoxy;

$R^3$ is hydrogen;

$R^4$, $R^5$ are hydrogen, $C_1$–$C_6$-alkyl, $C_1$–$C_6$-haloalkyl, $C_1$–$C_6$-alkoxy or $C_1$–$C_6$-haloalkoxy, in particular hydrogen, $C_1$–$C_6$-alkyl or $C_1$–$C_6$-alkoxy; particularly preferably hydrogen or $C_1$–$C_6$-alkyl such as methyl or ethyl; or $R^4$ and $R^5$ together form an —O—$(CH_2)_m$—O—, —O—$(CH_2)_m$—S— or —S—$(CH_2)_m$—S— chain, which may be substituted by one to three radicals selected from the following group: $C_1$–$C_4$-alkyl or $C_1$–$C_4$-haloalkyl; or $R^4$ and $R^5$ together form a —$(CH_2)_p$— chain which may be substituted by one to four radicals selected from the following group:

halogen, $C_1$–$C_4$-alkyl or $C_1$–$C_4$-haloalkyl; or $R^4$ and $R^5$ together form a methylidene group which may be substituted by one to two radicals selected from the following group:

halogen, cyano, $C_1$–$C_6$-alkyl, $C_1$–$C_6$-haloalkyl $C_1$–$C_6$-alkoxy or $C_1$–$C_6$-haloalkoxy;

l is 0;

m is 2 to 4; in particular 2 or 3 p is 2 to 5;

$R^7$ is a compound Ia or IIb

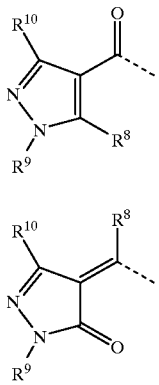

where
$R^8$ is halogen, $OR^{11}$, $SR^{11}$, $SO_2R^{12}$, $NR^{14}R^{15}$, $ONR^{15}R^{15}$, N-bonded heterocyclyl or O-(N-bonded heterocyclyl), where the heterocyclyl radical of the two lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^9$ is $C_1$–$C_6$-alkyl;
$R^{10}$ hydrogen or $C_1$–$C_6$-alkyl;
$R^{11}$ is $C_1$–$C_6$-alkyl, $C_3$–$C_6$-alkenyl, $C_3$–$C_6$-haloalkenyl, $C_3$–$C_6$-alkynyl, $C_1$–$C_{20}$-alkylcarbonyl, $C_3$–$C_6$-cycloalkylcarbonyl, $C_1$–$C_6$-alkoxycarbonyl, $C_3$–$C_6$-alkenyloxycarbonyl, $C_1$–$C_6$-alkylaminocarbonyl, $C_3$–$C_6$-alkenylaminocarbonyl, N,N-di-($C_1$–$C_6$-alkyl)aminocarbonyl, N-($C_3$–$C_6$-alkenyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy) aminocarbonyl, di-($C_1$–$C_6$-alkyl)aminothiocarbonyl or $C_1$–$C_6$-alkylcarbonyl-$C_1$–$C_6$-alkyl, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_{1-6}$-alkyl, phenylcarbonyl, heterocyclylcarbonyl, phenoxycarbonyl, phenyloxythiocarbonyl, heterocyclyloxycarbonyl or heterocyclyloxythiocarbonyl, where the phenyl and the heterocyclyl radical of the 12 lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy, $C_1$–$C_4$-haloalkoxy, heterocyclyl or N-bonded heterocyclyl, where the two lastmentioned substituents for their part may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^{12}$, $R^{13}$ are $C_1$–$C_6$-alkyl, $C_3$–$C_6$-alkenyl, $C_3$–$C_6$-haloalkenyl, $C_3$–$C_6$-cycloalkyl, hydroxyl, $C_1$–$C_6$-alkoxy or di-($C_1$–$C_6$-haloalkyl)amino, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
are phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^{14}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di-($C_1$–$C_6$-alkyl)amino, where the abovementioned alkyl, cycloalkyl and alkoxy radicals may be partially or fully halogenated and/or may carry one to three radicals of the following group:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^{15}$ is $C_1$–$C_6$-alkyl or $C_3$–$C_6$-alkenyl.

Particular preference is given to compounds of the formula I, where
$R^4$ is hydrogen, $C_1$–$C_6$-alkyl, $C_1$–$C_6$-haloalkyl, $C_1$–$C_6$-alkoxy or $C_1$–$C_6$-haloalkoxy; particularly preferably hydrogen, $C_1$–$C_6$-alkyl such as methyl or ethyl or $C_1$–$C_6$-alkoxy such as methoxy or ethoxy;
$R^5$ is hydrogen or $C_1$–$C_6$-alkyl; particularly preferably hydrogen or methyl; or
$R^4$ and $R^5$ together form an —O—$(CH_2)_2$—O—, —O—$(CH_2)_3$—O—, —O—$(CH_2)_2$—S—, —O—$(CH_2)_3$—S—, —S—$(CH_2)_2$—S—, —S—$(CH_2)_3$—S—, —$(CH_2)_2$—, —$(CH_2)_4$— or —$(CH_2)_5$— chain which may be substituted by one to three $C_1$–$C_4$-alkyl or $C_1$–$C_4$-haloalkyl radicals; or
$R^4$ and $R^5$ together form a methylidene group which may be substituted by a radical selected from the following group: halogen such as chlorine or bromine, $C_1$–$C_6$-alkyl such as methyl or ethyl, $C_1$–$C_6$-haloalkyl such as chloro-methyl, fluoromethyl, dichloromethyl, difluoromethyl or trifluoromethyl, $C_1$–$C_6$-alkoxy such as methoxy or ethoxy.

Very particular preference is given to the compounds of the formula I, where
$R^4$ is hydrogen, $C_1$–$C_6$-alkyl, $C_1$–$C_6$-haloalkyl, $C_1$–$C_6$-alkoxy or $C_1$–$C_6$-haloalkoxy; particularly preferably hydrogen, $C_1$–$C_6$-alkyl such as methyl or ethyl or $C_1$–$C_6$-alkoxy such as methoxy or ethoxy;
$R^5$ is hydrogen or $C_1$–$C_6$-alkyl; particularly preferably hydrogen or methyl.

Likewise, particular preference is given to compounds of the formula I, where $R^8$ is $NR^{14}R^{15}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

Very particular preference is given to compounds of the formula I, where $R^8$ is $NR^{14}R^{15}$ or tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydrothiazol-2-yl, tetrahydroimidazol-1-yl, tetrahydrooxazol-3-yl, tetrahydrothiazol-3-yl, pyrazol-1-yl, imidazol-1-yl, 1,2,4-triazol-1-yl, tetrazol-1-yl, piperidin-1-yl, hexahydropyrimidin-1-yl, hexahydropyrazin-1-yl, tetrahydro-1,4-oxazin-4-yl, tetrahydro-1,2-oxazin-2-yl, succinimide, maleinimide or glutarimide, where the abovementioned heterocycles may be partially or fully halogenated and/or may carry one to three of the following radicals: nitro, cyano, $C_1$–$C_4$-alkyl, such as methyl or ethyl, $C_1$–$C_4$-haloalkyl such as chloromethyl, difluoromethyl or trifluoromethyl, $C_1$–$C_4$-alkoxy such as methoxy or ethoxy or $C_1$–$C_4$-haloalkoxy such as difluoromethoxy or trifluoromethoxy.

Particular preference is also given to the compounds of the formula I in which $R^8$ is $OR^{11}$.

Particular preference is given to compounds of the formula I where $R^8$ is $OR^{11}$ and $R^{11}$ is $C_1$–$C_{20}$-alkylcarbonyl, $C_2$–$C_{20}$-alkenylcarbonyl, $C_2$–$C_6$-alkynylcarbonyl, $C_3$–$C_6$-cycloalkylcarbonyl or (2-norbornyl)methylcarbonyl, where the abovementioned alkyl and cycloalkyl radicals may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

is phenylcarbonyl-$C_1$–$C_6$-alkyl, heterocyclylcarbonyl-$C_1$–$C_6$-alkyl, phenylcarbonyl or heterocyclylcarbonyl, where the phenyl and the heterocyclyl radical of the 4 lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy, phenoxy, heterocyclyl or N-bonded heterocyclyl, where the three lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

Particular importance is given to the compounds of the formula I where $R^8$ is $OR^{11}$ and $R^{11}$ is $C_1$–$C_{20}$-alkylcarbonyl, $C_2$–$C_6$-alkenylcarbonyl, $C_2$–$C_6$-alkynylcarbonyl or $C_3$–$C_6$-cycloalkylcarbonyl, where the abovementioned alkyl and cycloalkyl radicals may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl) aminocarbonyl, aminocarbonyl, $C_1$–$C_4$-alkylcarbonyloxy or $C_3$–$C_6$-cycloalkyl;

is phenylcarbonyl-$C_1$–$C_6$-alkyl, heterocyclylcarbonyl-$C_1$–$C_6$-alkyl, phenylcarbonyl or heterocyclylcarbonyl, where the phenyl and the heterocyclyl radical of the 4 lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy, heterocyclyl or N-bonded heterocyclyl, where the two lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

Particular preference is also given to the compounds of the formula Ia.

Furthermore, particular preference is given to the compounds I where

X is $S(=O)_2$ or $CR^4R^5$;

$R^1$ is halogen or $C_1$–$C_6$-alkyl; in particular $C_1$–$C_4$-alkyl such as methyl or ethyl;

$R^3$ is hydrogen;

$R^4$ is hydrogen or $C_1$–$C_6$-alkyl; in particular $C_1$–$C_4$-Alkyl such as methyl or ethyl;

$R^5$ is hydrogen or $C_1$–$C_6$-alkyl; in particular $C_1$–$C_4$-alkyl such as methyl or ethyl;

l is 0;

$R^7$ is a compound IIa;

$R^8$ is halogen, such as chlorine or bromine, or $OR^{11}$;

$R^9$ is $C_1$–$C_6$-alkyl; in particular $C_1$–$C_4$-alkyl;

$R^{10}$ is hydrogen or $C_1$–$C_6$-alkyl; in particular hydrogen or $C_1$–$C_4$-alkyl such as methyl or ethyl;

$R^{11}$ is $C_1$–$C_{20}$-alkylcarbonyl, $C_2$–$C_{20}$-alkenylcarbonyl or (2-norbornyl)methylcarbonyl, where the alkyl radical may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl or $C_3$–$C_6$-cycloalkyl;

is phenylcarbonyl-$C_1$–$C_6$-alkyl, phenylcarbonyl or heterocyclylcarbonyl, where the phenyl and the heterocyclyl radical of the three lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, phenoxy, heterocyclyl or N-bonded heterocyclyl, where the three lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

Extraordinary preference is given to the compounds of the formula Ia1 and Ib1 ($\equiv$I where X=$C(CH_3)_2$ and l=0), in particular to the compounds Ia1.1 to Ia1.522 and the compounds Ib1.1 to Ib1.522, where the radical definitions $R^1$ to $R^{10}$ and l not only in combination with one another, but in each case also on their own, have a particular meaning for the compounds according to the invention.

TABLE 1

Structures Ia1 and Ib1 (pyrazole-thiochromanone sulfone derivatives)

| No. | | R¹ | R³ | R⁸ | R⁹ | R¹⁰ |
|---|---|---|---|---|---|---|
| Ia1.1 | or Ib1.1 | $CH_3$ | H | F | $CH_3$ | H |
| Ia1.2 | or Ib1.2 | $CH_3$ | H | Cl | $CH_3$ | H |
| Ia1.3 | or Ib1.3 | $CH_3$ | H | Br | $CH_3$ | H |
| Ia1.4 | or Ib1.4 | $CH_3$ | H | I | $CH_3$ | H |
| Ia1.5 | or Ib1.5 | $CH_3$ | H | $SO_2CH_3$ | $CH_3$ | H |
| Ia1.6 | or Ib1.6 | $CH_3$ | H | $SO_2CH_2CH_3$ | $CH_3$ | H |
| Ia1.7 | or Ib1.7 | $CH_3$ | H | $SC_6H_5$ | $CH_3$ | H |
| Ia1.8 | or Ib1.8 | $CH_3$ | H | S(4-$CH_3$—$C_6H_4$) | $CH_3$ | H |
| Ia1.9 | or Ib1.9 | $CH_3$ | H | S(4-Cl—$C_6H_4$) | $CH_3$ | H |
| Ia1.10 | or Ib1.10 | $CH_3$ | H | $SO_2C_6H_5$ | $CH_3$ | H |
| Ia1.11 | or Ib1.11 | $CH_3$ | H | $SO_2$(4-$CH_3$—$C_6H_4$) | $CH_3$ | H |
| Ia1.12 | or Ib1.12 | $CH_3$ | H | $SO_2$(4-Cl—$C_6H_4$) | $CH_3$ | H |
| Ia1.13 | or Ib1.13 | $CH_3$ | H | 4-morpholinyl | $CH_3$ | H |
| Ia1.14 | or Ib1.14 | $CH_3$ | H | 1-pyrrolidinyl | $CH_3$ | H |
| Ia1.15 | or Ib1.15 | $CH_3$ | H | 1-(1,2,4-triazolyl) | $CH_3$ | H |
| Ia1.16 | or Ib1.16 | $CH_3$ | H | 1-imidazolyl | $CH_3$ | H |
| Ia1.17 | or Ib1.17 | $CH_3$ | H | $N(OCH_3)CH_3$ | $CH_3$ | H |
| Ia1.18 | or Ib1.18 | $CH_3$ | H | 2-tetrahydro-isoxazolyl | $CH_3$ | H |
| Ia1.19 | or Ib1.19 | $CH_3$ | H | $N(CH_3)N(CH_3)_2$ | $CH_3$ | H |
| Ia1.20 | or Ib1.20 | $CH_3$ | H | $N(CH_2CH=CH_2)N(CH_3)_2$ | $CH_3$ | H |
| Ia1.21 | or Ib1.21 | $CH_3$ | H | $OPO(OCH_3)_2$ | $CH_3$ | H |
| Ia1.22 | or Ib1.22 | $CH_3$ | H | $OPO(OCH_2CH_3)_2$ | $CH_3$ | H |
| Ia1.23 | or Ib1.23 | $CH_3$ | H | $OPO(OC_6H_5)_2$ | $CH_3$ | H |
| Ia1.24 | or Ib1.24 | $CH_3$ | H | $OPO(CH_3)_2$ | $CH_3$ | H |
| Ia1.25 | or Ib1.25 | $CH_3$ | H | $OPO(CH_2CH_3)_2$ | $CH_3$ | H |
| Ia1.26 | or Ib1.26 | $CH_3$ | H | $OPO(C_6H_5)_2$ | $CH_3$ | H |
| Ia1.27 | or Ib1.27 | $CH_3$ | H | $OPS(OCH_3)_2$ | $CH_3$ | H |
| Ia1.28 | or Ib1.28 | $CH_3$ | H | $OPS(OCH_2CH_3)_2$ | $CH_3$ | H |
| Ia1.29 | or Ib1.29 | $CH_3$ | H | $PO(OCH_3)_2$ | $CH_3$ | H |
| Ia1.30 | or Ib1.30 | $CH_3$ | H | $PO(OCH_2CH_3)_2$ | $CH_3$ | H |
| Ia1.31 | or Ib1.31 | $CH_3$ | H | $PO(C_6H_5)_2$ | $CH_3$ | H |
| Ia1.32 | or Ib1.32 | $CH_3$ | H | $OCH_2C_6H_5$ | $CH_3$ | H |
| Ia1.33 | or Ib1.33 | $CH_3$ | H | $OCH_2$(2-furyl) | $CH_3$ | H |
| Ia1.34 | or Ib1.34 | $CH_3$ | H | $OCH_2$(3-furyl) | $CH_3$ | H |
| Ia1.35 | or Ib1.35 | $CH_3$ | H | $OCOOCH_3$ | $CH_3$ | H |
| Ia1.36 | or Ib1.36 | $CH_3$ | H | $OCOOCH_2CH_3$ | $CH_3$ | H |
| Ia1.37 | or Ib1.37 | $CH_3$ | H | $OCOOCH(CH_3)_2$ | $CH_3$ | H |
| Ia1.38 | or Ib1.38 | $CH_3$ | H | $OCOOC_6H_5$ | $CH_3$ | H |
| Ia1.39 | or Ib1.39 | $CH_3$ | H | $OCOOC(CH_3)_3$ | $CH_3$ | H |
| Ia1.40 | or Ib1.40 | $CH_3$ | H | $OCSOC_6H_5$ | $CH_3$ | H |
| Ia1.41 | or Ib1.41 | $CH_3$ | H | $OCSN(CH_3)_2$ | $CH_3$ | H |
| Ia1.42 | or Ib1.42 | $CH_3$ | H | $OCON(CH_3)_2$ | $CH_3$ | H |
| Ia1.43 | or Ib1.43 | $CH_3$ | H | $OCOSCH_3$ | $CH_3$ | H |
| Ia1.44 | or Ib1.44 | $CH_3$ | H | $ON(CH_3)_2$ | $CH_3$ | H |
| Ia1.45 | or Ib1.45 | $CH_3$ | H | O-1-piperidyl | $CH_3$ | H |
| Ia1.46 | or Ib1.46 | $CH_3$ | H | $OCO(CH_2)_2CH_3$ | $CH_3$ | H |
| Ia1.47 | or Ib1.47 | $CH_3$ | H | $OCO(CH_2)_6CH_3$ | $CH_3$ | H |
| Ia1.48 | or Ib1.48 | $CH_3$ | H | $OCO(CH_2)_7CH_3$ | $CH_3$ | H |
| Ia1.49 | or Ib1.49 | $CH_3$ | H | $OCO(CH_2)_{16}CH_3$ | $CH_3$ | H |
| Ia1.50 | or Ib1.50 | $CH_3$ | H | $OCO(CH_2)_{14}CH_3$ | $CH_3$ | H |
| Ia1.51 | or Ib1.51 | $CH_3$ | H | $OCOCH_2CH_2CH=CH_2$ | $CH_3$ | H |
| Ia1.52 | or Ib1.52 | $CH_3$ | H | OCOcyclopropyl | $CH_3$ | H |
| Ia1.53 | or Ib1.53 | $CH_3$ | H | OCOcyclopentyl | $CH_3$ | H |
| Ia1.54 | or Ib1.54 | $CH_3$ | H | OCOcyclohexyl | $CH_3$ | H |
| Ia1.55 | or Ib1.55 | $CH_3$ | H | OCO(2-tetrahydro-furyl) | $CH_3$ | H |
| Ia1.56 | or Ib1.56 | $CH_3$ | H | OCO(2-furyl) | $CH_3$ | H |
| Ia1.57 | or Ib1.57 | $CH_3$ | H | OCO(2-thienyl) | $CH_3$ | H |
| Ia1.58 | or Ib1.58 | $CH_3$ | H | OCO(3-pyridyl) | $CH_3$ | H |
| Ia1.59 | or Ib1.59 | $CH_3$ | H | F | $CH_2CH_3$ | H |
| Ia1.60 | or Ib1.60 | $CH_3$ | H | Cl | $CH_2CH_3$ | H |
| Ia1.61 | or Ib1.61 | $CH_3$ | H | Br | $CH_2CH_3$ | H |
| Ia1.62 | or Ib1.62 | $CH_3$ | H | I | $CH_2CH_3$ | H |

TABLE 1-continued

Structures Ia1 and Ib1 (pyrazole-carbonyl thiochroman sulfone derivatives)

| No. | | $R^1$ | $R^3$ | $R^8$ | $R^9$ | $R^{10}$ |
|---|---|---|---|---|---|---|
| Ia1.63 | or Ib1.63 | $CH_3$ | H | $SO_2CH_3$ | $CH_2CH_3$ | H |
| Ia1.64 | or Ib1.64 | $CH_3$ | H | $SO_2CH_2CH_3$ | $CH_2CH_3$ | H |
| Ia1.65 | or Ib1.65 | $CH_3$ | H | $SC_6H_5$ | $CH_2CH_3$ | H |
| Ia1.66 | or Ib1.66 | $CH_3$ | H | $S(4\text{-}CH_3\text{—}C_6H_4)$ | $CH_2CH_3$ | H |
| Ia1.67 | or Ib1.67 | $CH_3$ | H | $S(4\text{-}Cl\text{—}C_6H_4)$ | $CH_2CH_3$ | H |
| Ia1.68 | or Ib1.68 | $CH_3$ | H | $SO_2C_6H_5$ | $CH_2CH_3$ | H |
| Ia1.69 | or Ib1.69 | $CH_3$ | H | $SO_2(4\text{-}CH_3\text{—}C_6H_4)$ | $CH_2CH_3$ | H |
| Ia1.70 | or Ib1.70 | $CH_3$ | H | $SO_2(4\text{-}Cl\text{—}C_6H_4)$ | $CH_2CH_3$ | H |
| Ia1.71 | or Ib1.71 | $CH_3$ | H | 4-morpholinyl | $CH_2CH_3$ | H |
| Ia1.72 | or Ib1.72 | $CH_3$ | H | 1-pyrrolidinyl | $CH_2CH_3$ | H |
| Ia1.73 | or Ib1.73 | $CH_3$ | H | 1-(1,2,4-triazolyl) | $CH_2CH_3$ | H |
| Ia1.74 | or Ib1.74 | $CH_3$ | H | 1-imidazolyl | $CH_2CH_3$ | H |
| Ia1.75 | or Ib1.75 | $CH_3$ | H | $N(OCH_3)CH_3$ | $CH_2CH_3$ | H |
| Ia1.76 | or Ib1.76 | $CH_3$ | H | 2-tetrahydro-isoxazolyl | $CH_2CH_3$ | H |
| Ia1.77 | or Ib1.77 | $CH_3$ | H | $N(CH_3)N(CH_3)_2$ | $CH_2CH_3$ | H |
| Ia1.78 | or Ib1.78 | $CH_3$ | H | $N(CH_2CH{=}CH_2)N(CH_3)_2$ | $CH_2CH_3$ | H |
| Ia1.79 | or Ib1.79 | $CH_3$ | H | $OPO(OCH_3)_2$ | $CH_2CH_3$ | H |
| Ia1.80 | or Ib1.80 | $CH_3$ | H | $OPO(OCH_2CH_3)_2$ | $CH_2CH_3$ | H |
| Ia1.81 | or Ib1.81 | $CH_3$ | H | $OPO(OC_6H_5)_2$ | $CH_2CH_3$ | H |
| Ia1.82 | or Ib1.82 | $CH_3$ | H | $OPO(CH_3)_2$ | $CH_2CH_3$ | H |
| Ia1.83 | or Ib1.83 | $CH_3$ | H | $OPO(CH_2CH_3)_2$ | $CH_2CH_3$ | H |
| Ia1.84 | or Ib1.84 | $CH_3$ | H | $OPO(C_6H_5)_2$ | $CH_2CH_3$ | H |
| Ia1.85 | or Ib1.85 | $CH_3$ | H | $OPS(OCH_3)_2$ | $CH_2CH_3$ | H |
| Ia1.86 | or Ib1.86 | $CH_3$ | H | $OPS(OCH_2CH_3)_2$ | $CH_2CH_3$ | H |
| Ia1.87 | or Ib1.87 | $CH_3$ | H | $PO(OCH_3)_2$ | $CH_2CH_3$ | H |
| Ia1.88 | or Ib1.88 | $CH_3$ | H | $PO(OCH_2CH_3)_2$ | $CH_2CH_3$ | H |
| Ia1.89 | or Ib1.89 | $CH_3$ | H | $PO(C_6H_5)_2$ | $CH_2CH_3$ | H |
| Ia1.90 | or Ib1.90 | $CH_3$ | H | $OCH_2C_6H_5$ | $CH_2CH_3$ | H |
| Ia1.91 | or Ib1.91 | $CH_3$ | H | $OCH_2(2\text{-furyl})$ | $CH_2CH_3$ | H |
| Ia1.92 | or Ib1.92 | $CH_3$ | H | $OCH_2(3\text{-furyl})$ | $CH_2CH_3$ | H |
| Ia1.93 | or Ib1.93 | $CH_3$ | H | $OCOOCH_3$ | $CH_2CH_3$ | H |
| Ia1.94 | or Ib1.94 | $CH_3$ | H | $OCOOCH_2CH_3$ | $CH_2CH_3$ | H |
| Ia1.95 | or Ib1.95 | $CH_3$ | H | $OCOOCH(CH_3)_2$ | $CH_2CH_3$ | H |
| Ia1.96 | or Ib1.96 | $CH_3$ | H | $OCOOC_6H_5$ | $CH_2CH_3$ | H |
| Ia1.97 | or Ib1.97 | $CH_3$ | H | $OCOOC(CH_3)_3$ | $CH_2CH_3$ | H |
| Ia1.98 | or Ib1.98 | $CH_3$ | H | $OCSOC_6H_5$ | $CH_2CH_3$ | H |
| Ia1.99 | or Ib1.99 | $CH_3$ | H | $OCSN(CH_3)_2$ | $CH_2CH_3$ | H |
| Ia1.100 | or Ib1.100 | $CH_3$ | H | $OCON(CH_3)_2$ | $CH_2CH_3$ | H |
| Ia1.101 | or Ib1.101 | $CH_3$ | H | $OCOSCH_3$ | $CH_2CH_3$ | H |
| Ia1.102 | or Ib1.102 | $CH_3$ | H | $ON(CH_3)_2$ | $CH_2CH_3$ | H |
| Ia1.103 | or Ib1.103 | $CH_3$ | H | O-1-piperidyl | $CH_2CH_3$ | H |
| Ia1.104 | or Ib1.104 | $CH_3$ | H | $OCO(CH_2)_2CH_3$ | $CH_2CH_3$ | H |
| Ia1.105 | or Ib1.105 | $CH_3$ | H | $OCO(CH_2)_6CH_3$ | $CH_2CH_3$ | H |
| Ia1.106 | or Ib1.106 | $CH_3$ | H | $OCO(CH_2)_7CH_3$ | $CH_2CH_3$ | H |
| Ia1.107 | or Ib1.107 | $CH_3$ | H | $OCO(CH_2)_{16}CH_3$ | $CH_2CH_3$ | H |
| Ia1.108 | or Ib1.108 | $CH_3$ | H | $OCO(CH_2)_{14}CH_3$ | $CH_2CH_3$ | H |
| Ia1.109 | or Ib1.109 | $CH_3$ | H | $OCOCH_2CH_2CH{=}CH_2$ | $CH_2CH_3$ | H |
| Ia1.110 | or Ib1.110 | $CH_3$ | H | OCOcyclopropyl | $CH_2CH_3$ | H |
| Ia1.111 | or Ib1.111 | $CH_3$ | H | OCOcyclopentyl | $CH_2CH_3$ | H |
| Ia1.112 | or Ib1.112 | $CH_3$ | H | OCOcyclohexyl | $CH_2CH_3$ | H |
| Ia1.113 | or Ib1.113 | $CH_3$ | H | OCO(2-tetrahydro-furyl) | $CH_2CH_3$ | H |
| Ia1.114 | or Ib1.114 | $CH_3$ | H | OCO(2-furyl) | $CH_2CH_3$ | H |
| Ia1.115 | or Ib1.115 | $CH_3$ | H | OCO(2-thienyl) | $CH_2CH_3$ | H |
| Ia1.116 | or Ib1.116 | $CH_3$ | H | OCO(3-pyridyl) | $CH_2CH_3$ | H |
| Ia1.117 | or Ib1.117 | $CH_3$ | H | F | $CH_3$ | $CH_3$ |
| Ia1.118 | or Ib1.118 | $CH_3$ | H | Cl | $CH_3$ | $CH_3$ |
| Ia1.119 | or Ib1.119 | $CH_3$ | H | Br | $CH_3$ | $CH_3$ |
| Ia1.120 | or Ib1.120 | $CH_3$ | H | I | $CH_3$ | $CH_3$ |
| Ia1.121 | or Ib1.121 | $CH_3$ | H | $SO_2CH_3$ | $CH_3$ | $CH_3$ |
| Ia1.122 | or Ib1.122 | $CH_3$ | H | $SO_2CH_2CH_3$ | $CH_3$ | $CH_3$ |
| Ia1.123 | or Ib1.123 | $CH_3$ | H | $SC_6H_5$ | $CH_3$ | $CH_3$ |
| Ia1.124 | or Ib1.124 | $CH_3$ | H | $S(4\text{-}CH_3\text{—}C_6H_4)$ | $CH_3$ | $CH_3$ |

TABLE 1-continued

Structures Ia1 and Ib1 (pyrazole/sulfone derivatives)

| No. | | R¹ | R³ | R⁸ | R⁹ | R¹⁰ |
|---|---|---|---|---|---|---|
| Ia1.125 | or Ib1.125 | CH₃ | H | S(4-Cl—C₆H₄) | CH₃ | CH₃ |
| Ia1.126 | or Ib1.126 | CH₃ | H | CO₂C₆H₅ | CH₃ | CH₃ |
| Ia1.127 | or Ib1.127 | CH₃ | H | CO₂(4-CH₃—C₆H₄) | CH₃ | CH₃ |
| Ia1.128 | or Ib1.128 | CH₃ | H | CO₂(4-Cl—C₆H₄) | CH₃ | CH₃ |
| Ia1.129 | or Ib1.129 | CH₃ | H | 4-morpholinyl | CH₃ | CH₃ |
| Ia1.130 | or Ib1.130 | CH₃ | H | 1-pyrrolidinyl | CH₃ | CH₃ |
| Ia1.131 | or Ib1.131 | CH₃ | H | 1-(1,2,4-triazolyl) | CH₃ | CH₃ |
| Ia1.132 | or Ib1.132 | CH₃ | H | 1-imidazolyl | CH₃ | CH₃ |
| Ia1.133 | or Ib1.133 | CH₃ | H | N(OCH₃)CH₃ | CH₃ | CH₃ |
| Ia1.134 | or Ib1.134 | CH₃ | H | 2-tetrahydro-isoxazolyl | CH₃ | CH₃ |
| Ia1.135 | or Ib1.135 | CH₃ | H | N(CH₃)N(CH₃)₂ | CH₃ | CH₃ |
| Ia1.136 | or Ib1.136 | CH₃ | H | N(CH₂CH=CH₂)N(CH₃)₂ | CH₃ | CH₃ |
| Ia1.137 | or Ib1.137 | CH₃ | H | OPO(OCH₃)₂ | CH₃ | CH₃ |
| Ia1.138 | or Ib1.138 | CH₃ | H | OPO(OCH₂CH₃)₂ | CH₃ | CH₃ |
| Ia1.139 | or Ib1.139 | CH₃ | H | OPO(OC₆H₅)₂ | CH₃ | CH₃ |
| Ia1.140 | or Ib1.140 | CH₃ | H | OPO(CH₃)₂ | CH₃ | CH₃ |
| Ia1.141 | or Ib1.141 | CH₃ | H | OPO(CH₂CH₃)₂ | CH₃ | CH₃ |
| Ia1.142 | or Ib1.142 | CH₃ | H | OPO(C₆H₅)₂ | CH₃ | CH₃ |
| Ia1.143 | or Ib1.143 | CH₃ | H | OPS(OCH₃)₂ | CH₃ | CH₃ |
| Ia1.144 | or Ib1.144 | CH₃ | H | OPS(OCH₂CH₃)₂ | CH₃ | CH₃ |
| Ia1.145 | or Ib1.145 | CH₃ | H | PO(OCH₃)₂ | CH₃ | CH₃ |
| Ia1.146 | or Ib1.146 | CH₃ | H | PO(OCH₂CH₃)₂ | CH₃ | CH₃ |
| Ia1.147 | or Ib1.147 | CH₃ | H | PO(C₆H₅)₂ | CH₃ | CH₃ |
| Ia1.148 | or Ib1.148 | CH₃ | H | OCH₂C₆H₅ | CH₃ | CH₃ |
| Ia1.149 | or Ib1.149 | OCH₃ | H | OCH₂(2-furyl) | CH₃ | CH₃ |
| Ia1.150 | or Ib1.150 | CH₃ | H | OCH₂(3-furyl) | CH₃ | CH₃ |
| Ia1.151 | or Ib1.151 | CH₃ | H | OCOOCH₃ | CH₃ | CH₃ |
| Ia1.152 | or Ib1.152 | CH₃ | H | OCOOCH₂CH₃ | CH₃ | CH₃ |
| Ia1.153 | or Ib1.153 | CH₃ | H | OCOOCH(CH₃)₂ | CH₃ | CH₃ |
| Ia1.154 | or Ib1.154 | CH₃ | H | OCOOC₆H₅ | CH₃ | CH₃ |
| Ia1.155 | or Ib1.155 | CH₃ | H | OCOOC(CH₃)₃ | CH₃ | CH₃ |
| Ia1.156 | or Ib1.156 | CH₃ | H | OCSOC₆H₅ | CH₃ | CH₃ |
| Ia1.157 | or Ib1.157 | CH₃ | H | OCSN(CH₃)₂ | CH₃ | CH₃ |
| Ia1.158 | or Ib1.158 | CH₃ | H | OCON(CH₃)₂ | CH₃ | CH₃ |
| Ia1.159 | or Ib1.159 | CH₃ | H | OCOSCH₃ | CH₃ | CH₃ |
| Ia1.160 | or Ib1.160 | CH₃ | H | ON(CH₃)₂ | CH₃ | CH₃ |
| Ia1.161 | or Ib1.161 | CH₃ | H | O-1-piperidyl | CH₃ | CH₃ |
| Ia1.162 | or Ib1.162 | CH₃ | H | OCO(CH₂)₂CH₃ | CH₃ | CH₃ |
| Ia1.163 | or Ib1.163 | CH₃ | H | OCO(CH₂)₆CH₃ | CH₃ | CH₃ |
| Ia1.164 | or Ib1.164 | CH₃ | H | OCO(CH₂)₇CH₃ | CH₃ | CH₃ |
| Ia1.165 | or Ib1.165 | CH₃ | H | OCO(CH₂)₁₆CH₃ | CH₃ | CH₃ |
| Ia1.166 | or Ib1.166 | CH₃ | H | OCO(CH₂)₁₄CH₃ | CH₃ | CH₃ |
| Ia1.167 | or Ib1.167 | CH₃ | H | OCOCH₂CH₂CH=CH₂ | CH₃ | CH₃ |
| Ia1.168 | or Ib1.168 | CH₃ | H | OCOcyclopropyl | CH₃ | CH₃ |
| Ia1.169 | or Ib1.169 | CH₃ | H | OCOcyclopentyl | CH₃ | CH₃ |
| Ia1.170 | or Ib1.170 | CH₃ | H | OCOcyclohexyl | CH₃ | CH₃ |
| Ia1.171 | or Ib1.171 | CH₃ | H | OCO(2-tetrahydro-furyl) | CH₃ | CH₃ |
| Ia1.172 | or Ib1.172 | CH₃ | H | OCO(2-furyl) | CH₃ | CH₃ |
| Ia1.173 | or Ib1.173 | CH₃ | H | OCO(2-thienyl) | CH₃ | CH₃ |
| Ia1.174 | or Ib1.174 | CH₃ | H | OCO(3-pyridyl) | CH₃ | CH₃ |
| Ia1.175 | or Ib1.175 | Cl | H | F | CH₃ | H |
| Ia1.176 | or Ib1.176 | Cl | H | Cl | CH₃ | H |
| Ia1.177 | or Ib1.177 | Cl | H | Br | CH₃ | H |
| Ia1.178 | or Ib1.178 | Cl | H | I | CH₃ | H |
| Ia1.179 | or Ib1.179 | Cl | H | SO₂CH₃ | CH₃ | H |
| Ia1.180 | or Ib1.180 | Cl | H | SO₂CH₂CH₃ | CH₃ | H |
| Ia1.181 | or Ib1.181 | Cl | H | SC₆H₅ | CH₃ | H |
| Ia1.182 | or Ib1.182 | Cl | H | S(4-CH₃—C₆H₄) | CH₃ | H |
| Ia1.183 | or Ib1.183 | Cl | H | S(4-Cl—C₆H₄) | CH₃ | H |
| Ia1.184 | or Ib1.184 | Cl | H | SO₂C₆H₅ | CH₃ | H |
| Ia1.185 | or Ib1.185 | Cl | H | SO₂(4-CH₃—C₆H₄) | CH₃ | H |
| Ia1.186 | or Ib1.186 | Cl | H | CO₂(4-Cl—C₆H₄) | CH₃ | H |

TABLE 1-continued

Structures Ia1 and Ib1 (pyrazole-substituted thiochromanone dioxides)

| No. | | R¹ | R³ | R⁸ | R⁹ | R¹⁰ |
|---|---|---|---|---|---|---|
| Ia1.187 | or Ib1.187 | Cl | H | 4-morpholinyl | $CH_3$ | H |
| Ia1.188 | or Ib1.188 | Cl | H | 1-pyrrolidinyl | $CH_3$ | H |
| Ia1.189 | or Ib1.189 | Cl | H | 1-(1,2,4-triazolyl) | $CH_3$ | H |
| Ia1.190 | or Ib1.190 | Cl | H | 1-imidazolyl | $CH_3$ | H |
| Ia1.191 | or Ib1.191 | Cl | H | $N(OCH_3)CH_3$ | $CH_3$ | H |
| Ia1.192 | or Ib1.192 | Cl | H | 2-tetrahydro-isoxazolyl | $CH_3$ | H |
| Ia1.193 | or Ib1.193 | Cl | H | $N(CH_3)N(CH_3)_2$ | $CH_3$ | H |
| Ia1.194 | or Ib1.194 | Cl | H | $N(CH_2CH=CH_2)N(CH_3)_2$ | $CH_3$ | H |
| Ia1.195 | or Ib1.195 | Cl | H | $OPO(OCH_3)_2$ | $CH_3$ | H |
| Ia1.196 | or Ib1.196 | Cl | H | $OPO(OCH_2CH_3)_2$ | $CH_3$ | H |
| Ia1.197 | or Ib1.197 | Cl | H | $OPO(OC_6H_5)_2$ | $CH_3$ | H |
| Ia1.198 | or Ib1.198 | Cl | H | $OPO(CH_3)_2$ | $CH_3$ | H |
| Ia1.199 | or Ib1.199 | Cl | H | $OPO(CH_2CH_3)_2$ | $CH_3$ | H |
| Ia1.200 | or Ib1.200 | Cl | H | $OPO(C_6H_5)_2$ | $CH_3$ | H |
| Ia1.201 | or Ib1.201 | Cl | H | $OPS(OCH_3)_2$ | $CH_3$ | H |
| Ia1.202 | or Ib1.202 | Cl | H | $OPS(OCH_2CH_3)_2$ | $CH_3$ | H |
| Ia1.203 | or Ib1.203 | Cl | H | $PO(OCH_3)_2$ | $CH_3$ | H |
| Ia1.204 | or Ib1.204 | Cl | H | $PO(OCH_2CH_3)_2$ | $CH_3$ | H |
| Ia1.205 | or Ib1.205 | Cl | H | $PO(C_6H_5)_2$ | $CH_3$ | H |
| Ia1.206 | or Ib1.206 | Cl | H | $OCH_2C_6H_5$ | $CH_3$ | H |
| Ia1.207 | or Ib1.207 | Cl | H | $OCH_2(2\text{-furyl})$ | $CH_3$ | H |
| Ia1.208 | or Ib1.208 | Cl | H | $OCH_2(3\text{-furyl})$ | $CH_3$ | H |
| Ia1.209 | or Ib1.209 | Cl | H | $OCOOCH_3$ | $CH_3$ | H |
| Ia1.210 | or Ib1.210 | Cl | H | $OCOOCH_2CH_3$ | $CH_3$ | H |
| Ia1.211 | or Ib1.211 | Cl | H | $OCOOCH(CH_3)_2$ | $CH_3$ | H |
| Ia1.212 | or Ib1.212 | Cl | H | $OCOOC_6H_5$ | $CH_3$ | H |
| Ia1.213 | or Ib1.213 | Cl | H | $OCOOC(CH_3)_3$ | $CH_3$ | H |
| Ia1.214 | or Ib1.214 | Cl | H | $OCSOC_6H_5$ | $CH_3$ | H |
| Ia1.215 | or Ib1.215 | Cl | H | $OCSN(CH_3)_2$ | $CH_3$ | H |
| Ia1.216 | or Ib1.216 | Cl | H | $OCON(CH_3)_2$ | $CH_3$ | H |
| Ia1.217 | or Ib1.217 | Cl | H | $OCOSCH_3$ | $CH_3$ | H |
| Ia1.218 | or Ib1.218 | Cl | H | $ON(CH_3)_2$ | $CH_3$ | H |
| Ia1.219 | or Ib1.219 | Cl | H | O-1-Piperidyl | $CH_3$ | H |
| Ia1.220 | or Ib1.220 | Cl | H | $OCO(CH_2)_2CH_3$ | $CH_3$ | H |
| Ia1.221 | or Ib1.221 | Cl | H | $OCO(CH_2)_6CH_3$ | $CH_3$ | H |
| Ia1.222 | or Ib1.222 | Cl | H | $OCO(CH_2)_7CH_3$ | $CH_3$ | H |
| Ia1.223 | or Ib1.223 | Cl | H | $OCO(CH_2)_{16}CH_3$ | $CH_3$ | H |
| Ia1.224 | or Ib1.224 | Cl | H | $OCO(CH_2)_{14}CH_3$ | $CH_3$ | H |
| Ia1.225 | or Ib1.225 | Cl | H | $OCOCH_2CH_2CH=CH_2$ | $CH_3$ | H |
| Ia1.226 | or Ib1.226 | Cl | H | OCOcyclopropyl | $CH_3$ | H |
| Ia1.227 | or Ib1.227 | Cl | H | OCOcyclopentyl | $CH_3$ | H |
| Ia1.228 | or Ib1.228 | Cl | H | OCOcyclohexyl | $CH_3$ | H |
| Ia1.229 | or Ib1.229 | Cl | H | OCO(2-tetrahydrofuryl) | $CH_3$ | H |
| Ia1.230 | or Ib1.230 | Cl | H | OCO(2-furyl) | $CH_3$ | H |
| Ia1.231 | or Ib1.231 | Cl | H | OCO(2-thienyl) | $CH_3$ | H |
| Ia1.232 | or Ib1.232 | Cl | H | OCO(3-pyridyl) | $CH_3$ | H |
| Ia1.233 | or Ib1.233 | Cl | H | F | $CH_2CH_3$ | H |
| Ia1.234 | or Ib1.234 | Cl | H | Cl | $CH_2CH_3$ | H |
| Ia1.235 | or Ib1.235 | Cl | H | Br | $CH_2CH_3$ | H |
| Ia1.236 | or Ib1.236 | Cl | H | I | $CH_2CH_3$ | H |
| Ia1.237 | or Ib1.237 | Cl | H | $SO_2CH_3$ | $CH_2CH_3$ | H |
| Ia1.238 | or Ib1.238 | Cl | H | $SO_2CH_2CH_3$ | $CH_2CH_3$ | H |
| Ia1.239 | or Ib1.239 | Cl | H | $SC_6H_5$ | $CH_2CH_3$ | H |
| Ia1.240 | or Ib1.240 | Cl | H | $S(4\text{-}CH_3\text{—}C_6H_4)$ | $CH_2CH_3$ | H |
| Ia1.241 | or Ib1.241 | Cl | H | $S(4\text{-}Cl\text{—}C_6H_4)$ | $CH_2CH_3$ | H |
| Ia1.242 | or Ib1.242 | Cl | H | $SO_2C_6H_5$ | $CH_2CH_3$ | H |
| Ia1.243 | or Ib1.243 | Cl | H | $SO_2(4\text{-}CH_3\text{—}C_6H_4)$ | $CH_2CH_3$ | H |
| Ia1.244 | or Ib1.244 | Cl | H | $SO_2(4\text{-}Cl\text{—}C_6H_4)$ | $CH_2CH_3$ | H |
| Ia1.245 | or Ib1.245 | Cl | H | 4-morpholinyl | $CH_2CH_3$ | H |
| Ia1.246 | or Ib1.246 | Cl | H | 1-pyrrolidinyl | $CH_2CH_3$ | H |
| Ia1.247 | or Ib1.247 | Cl | H | 1-(1,2,4-triazolyl) | $CH_2CH_3$ | H |
| Ia1.248 | or Ib1.248 | Cl | H | i-imidazolyl | $CH_2CH_3$ | H |

TABLE 1-continued

Ia1 / Ib1 structures (pyrazole-carbonyl-thiochromane sulfone scaffolds)

| No. | | $R^1$ | $R^3$ | $R^8$ | $R^9$ | $R^{10}$ |
|---|---|---|---|---|---|---|
| Ia1.249 | or Ib1.249 | Cl | H | N(OCH$_3$)CH$_3$ | CH$_2$CH$_3$ | H |
| Ia1.250 | or Ib1.250 | Cl | H | 2-tetrahydro-isoxazolyl | CH$_2$CH$_3$ | H |
| Ia1.251 | or Ib1.251 | Cl | H | N(CH$_3$)N(CH$_3$)$_2$ | CH$_2$CH$_3$ | H |
| Ia1.252 | or Ib1.252 | Cl | H | N(CH$_2$CH=CH$_2$)N(CH$_3$)$_2$ | CH$_2$CH$_3$ | H |
| Ia1.253 | or Ib1.253 | Cl | H | OPO(OCH$_3$)$_2$ | CH$_2$CH$_3$ | H |
| Ia1.254 | or Ib1.254 | Cl | H | OPO(OCH$_2$CH$_3$)$_2$ | CH$_2$CH$_3$ | H |
| Ia1.255 | or Ib1.255 | Cl | H | OPO(OC$_6$H$_5$)$_2$ | CH$_2$CH$_3$ | H |
| Ia1.256 | or Ib1.256 | Cl | H | OPO(CH$_3$)$_2$ | CH$_2$CH$_3$ | H |
| Ia1.257 | or Ib1.257 | Cl | H | OPO(CH$_2$CH$_3$)$_2$ | CH$_2$CH$_3$ | H |
| Ia1.258 | or Ib1.258 | Cl | H | OPO(C$_6$H$_5$)$_2$ | CH$_2$CH$_3$ | H |
| Ia1.259 | or Ib1.259 | Cl | H | OPS(OCH$_3$)$_2$ | CH$_2$CH$_3$ | H |
| Ia1.260 | or Ib1.260 | Cl | H | OPS(OCH$_2$CH$_3$)$_2$ | CH$_2$CH$_3$ | H |
| Ia1.261 | or Ib1.261 | Cl | H | PO(OCH$_3$)$_2$ | CH$_2$CH$_3$ | H |
| Ia1.262 | or Ib1.262 | Cl | H | PO(OCH$_2$CH$_3$)$_2$ | CH$_2$CH$_3$ | H |
| Ia1.263 | or Ib1.263 | Cl | H | PO(C$_6$H$_5$)$_2$ | CH$_2$CH$_3$ | H |
| Ia1.264 | or Ib1.264 | Cl | H | OCH$_2$C$_6$H$_5$ | CH$_2$CH$_3$ | H |
| Ia1.265 | or Ib1.265 | Cl | H | OCH$_2$(2-furyl) | CH$_2$CH$_3$ | H |
| Ia1.266 | or Ib1.266 | Cl | H | OCH$_2$(3-furyl) | CH$_2$CH$_3$ | H |
| Ia1.267 | or Ib1.267 | Cl | H | OCOOCH$_3$ | CH$_2$CH$_3$ | H |
| Ia1.268 | or Ib1.268 | Cl | H | OCOOCH$_2$CH$_3$ | CH$_2$CH$_3$ | H |
| Ia1.269 | or Ib1.269 | Cl | H | OCOOCH(CH$_3$)$_2$ | CH$_2$CH$_3$ | H |
| Ia1.270 | or Ib1.270 | Cl | H | OCOOC$_6$H$_5$ | CH$_2$CH$_3$ | H |
| Ia1.271 | or Ib1.271 | Cl | H | OCOOC(CH$_3$)$_3$ | CH$_2$CH$_3$ | H |
| Ia1.272 | or Ib1.272 | Cl | H | OCSOC$_6$H$_5$ | CH$_2$CH$_3$ | H |
| Ia1.273 | or Ib1.273 | Cl | H | OCSN(CH$_3$)$_2$ | CH$_2$CH$_3$ | H |
| Ia1.274 | or Ib1.274 | Cl | H | OCON(CH$_3$)$_2$ | CH$_2$CH$_3$ | H |
| Ia1.275 | or Ib1.275 | Cl | H | OCOSCH$_3$ | CH$_2$CH$_3$ | H |
| Ia1.276 | or Ib1.276 | Cl | H | ON(CH$_3$)$_2$ | CH$_2$CH$_3$ | H |
| Ia1.277 | or Ib1.277 | Cl | H | O-1-piperidyl | CH$_2$CH$_3$ | H |
| Ia1.278 | or Ib1.278 | Cl | H | OCO(CH$_2$)$_2$CH$_3$ | CH$_2$CH$_3$ | H |
| Ia1.279 | or Ib1.279 | Cl | H | CCO(CH$_2$)$_6$CH$_3$ | CH$_2$CH$_3$ | H |
| Ia1.280 | or Ib1.280 | Cl | H | OCO(CH$_2$)$_7$CH$_3$ | CH$_2$CH$_3$ | H |
| Ia1.281 | or Ib1.281 | Cl | H | OCO(CH$_2$)$_{16}$CH$_3$ | CH$_2$CH$_3$ | H |
| Ia1.282 | or Ib1.282 | Cl | H | OCO(CH$_2$)$_{14}$CH$_3$ | CH$_2$CH$_3$ | H |
| Ia1.283 | or Ib1.283 | Cl | H | OCOCH$_2$CH$_2$CH=CH$_2$ | CH$_2$CH$_3$ | H |
| Ia1.284 | or Ib1.284 | Cl | H | OCOcyclopropyl | CH$_2$CH$_3$ | H |
| Ia1.285 | or Ib1.285 | Cl | H | OCOcyclopentyl | CH$_2$CH$_3$ | H |
| Ia1.286 | or Ib1.286 | Cl | H | OCOcyclohexyl | CH$_2$CH$_3$ | H |
| Ia1.287 | or Ib1.287 | Cl | H | OCO(2-tetra-hydrofuryl) | CH$_2$CH$_3$ | H |
| Ia1.288 | or Ib1.288 | Cl | H | OCO(2-furyl) | CH$_2$CH$_3$ | H |
| Ia1.289 | or Ib1.289 | Cl | H | OCO(2-thienyl) | CH$_2$CH$_3$ | H |
| Ia1.290 | or Ib1.290 | Cl | H | OCO(3-pyridyl) | CH$_2$CH$_3$ | H |
| Ia1.291 | or Ib1.291 | Cl | H | F | CH$_3$ | CH$_3$ |
| Ia1.292 | or Ib1.292 | Cl | H | Cl | CH$_3$ | CH$_3$ |
| Ia1.293 | or Ib1.293 | Cl | H | Br | CH$_3$ | CH$_3$ |
| Ia1.294 | or Ib1.294 | Cl | H | I | CH$_3$ | CH$_3$ |
| Ia1.295 | or Ib1.295 | Cl | H | SO$_2$CH$_3$ | CH$_3$ | CH$_3$ |
| Ia1.296 | or Ib1.296 | Cl | H | SO$_2$CH$_2$CH$_3$ | CH$_3$ | CH$_3$ |
| Ia1.297 | or Ib1.297 | Cl | H | SC$_6$H$_5$ | CH$_3$ | CH$_3$ |
| Ia1.298 | or Ib1.298 | Cl | H | S(4-CH$_3$—C$_6$H$_4$) | CH$_3$ | CH$_3$ |
| Ia1.299 | or Ib1.299 | Cl | H | S(4-Cl—C$_6$H$_4$) | CH$_3$ | CH$_3$ |
| Ia1.300 | or Ib1.300 | Cl | H | SO$_2$C$_6$H$_5$ | CH$_3$ | CH$_3$ |
| Ia1.301 | or Ib1.301 | Cl | H | SO$_2$(4-CH$_3$—C$_6$H$_4$) | CH$_3$ | CH$_3$ |
| Ia1.302 | or Ib1.302 | Cl | H | SO$_2$(4-Cl—C$_6$H$_4$) | CH$_3$ | CH$_3$ |
| Ia1.303 | or Ib1.303 | Cl | H | 4-morpholinyl | CH$_3$ | CH$_3$ |
| Ia1.304 | or Ib1.304 | Cl | H | 1-pyrrolidinyl | CH$_3$ | CH$_3$ |
| Ia1.305 | or Ib1.305 | Cl | H | 1-(1,2,4-triazolyl) | CH$_3$ | CH$_3$ |
| Ia1.306 | or Ib1.306 | Cl | H | 1-imidazolyl | CH$_3$ | CH$_3$ |
| Ia1.307 | or Ib1.307 | Cl | H | N(OCH$_3$)CH$_3$ | CH$_3$ | CH$_3$ |
| Ia1.308 | or Ib1.308 | Cl | H | 2-tetrahydro-isoxazolyl | CH$_3$ | CH$_3$ |
| Ia1.309 | or Ib1.309 | Cl | H | N(CH$_3$)N(CH$_3$)$_2$ | CH$_3$ | CH$_3$ |

TABLE 1-continued

Ia1

Ib1

| No. | | R¹ | R³ | R⁸ | R⁹ | R¹⁰ |
|---|---|---|---|---|---|---|
| Ia1.310 | or Ib1.310 | Cl | H | N(CH$_2$CH=CH$_2$)N(CH$_3$)$_2$ | CH$_3$ | CH$_3$ |
| Ia1.311 | or Ib1.311 | Cl | H | OPO(OCH$_3$)$_2$ | CH$_3$ | CH$_3$ |
| Ia1.312 | or Ib1.312 | Cl | H | OPO(OCH$_2$CH$_3$)$_2$ | CH$_3$ | CH$_3$ |
| Ia1.313 | or Ib1.313 | Cl | H | OPO(OC$_6$H$_5$)$_2$ | CH$_3$ | CH$_3$ |
| Ia1.314 | or Ib1.314 | Cl | H | OPO(CH$_3$)$_2$ | CH$_3$ | CH$_3$ |
| Ia1.315 | or Ib1.315 | Cl | H | OPO(CH$_2$CH$_3$)$_2$ | CH$_3$ | CH$_3$ |
| Ia1.316 | or Ib1.316 | Cl | H | OPO(C$_6$H$_5$)$_2$ | CH$_3$ | CH$_3$ |
| Ia1.317 | or Ib1.317 | Cl | H | OPS(OCH$_3$)$_2$ | CH$_3$ | CH$_3$ |
| Ia1.318 | or Ib1.318 | Cl | H | OPS(OCH$_2$CH$_3$)$_2$ | CH$_3$ | CH$_3$ |
| Ia1.319 | or Ib1.319 | Cl | H | PO(OCH$_3$)$_2$ | CH$_3$ | CH$_3$ |
| Ia1.320 | or Ib1.320 | Cl | H | PO(OCH$_2$CH$_3$)$_2$ | CH$_3$ | CH$_3$ |
| Ia1.321 | or Ib1.321 | Cl | H | PO(C$_6$H$_5$)$_2$ | CH$_3$ | CH$_3$ |
| Ia1.322 | or Ib1.322 | Cl | H | OCH$_2$C$_6$H$_5$ | CH$_3$ | CH$_3$ |
| Ia1.323 | or Ib1.323 | Cl | H | OCH$_2$(2-furyl) | CH$_3$ | CH$_3$ |
| Ia1.324 | or Ib1.324 | Cl | H | OCH$_2$(3-furyl) | CH$_3$ | CH$_3$ |
| Ia1.325 | or Ib1.325 | Cl | H | OCOOCH$_3$ | CH$_3$ | CH$_3$ |
| Ia1.326 | or Ib1.326 | Cl | H | OCOOCH$_2$CH$_3$ | CH$_3$ | CH$_3$ |
| Ia1.327 | or Ib1.327 | Cl | H | OCOOCH(CH$_3$)$_2$ | CH$_3$ | CH$_3$ |
| Ia1.328 | or Ib1.328 | Cl | H | OCOOC$_6$H$_5$ | CH$_3$ | CH$_3$ |
| Ia1.329 | or Ib1.329 | Cl | H | OCOOC(CH$_3$)$_3$ | CH$_3$ | CH$_3$ |
| Ia1.330 | or Ib1.330 | Cl | H | OCSOC$_6$H$_5$ | CH$_3$ | CH$_3$ |
| Ia1.331 | or Ib1.331 | Cl | H | OCSN(CH$_3$)$_2$ | CH$_3$ | CH$_3$ |
| Ia1.332 | or Ib1.332 | Cl | H | OCON(CH$_3$)$_2$ | CH$_3$ | CH$_3$ |
| Ia1.333 | or Ib1.333 | Cl | H | OCOSCH$_3$ | CH$_3$ | CH$_3$ |
| Ia1.334 | or Ib1.334 | Cl | H | ON(CH$_3$)$_2$ | CH$_3$ | CH$_3$ |
| Ia1.335 | or Ib1.335 | Cl | H | O-1-piperidyl | CH$_3$ | CH$_3$ |
| Ia1.336 | or Ib1.336 | Cl | H | OCO(CH$_2$)$_2$CH$_3$ | CH$_3$ | CH$_3$ |
| Ia1.337 | or Ib1.337 | Cl | H | OCO(CH$_2$)$_6$CH$_3$ | CH$_3$ | CH$_3$ |
| Ia1.338 | or Ib1.338 | Cl | H | OCO(CH$_2$)$_7$CH$_3$ | CH$_3$ | CH$_3$ |
| Ia1.339 | or Ib1.339 | Cl | H | OCO(CH$_2$)$_{16}$CH$_3$ | CH$_3$ | CH$_3$ |
| Ia1.340 | or Ib1.340 | Cl | H | OCO(CH$_2$)$_{14}$CH$_3$ | CH$_3$ | CH$_3$ |
| Ia1.341 | or Ib1.341 | Cl | H | OCOCH$_2$CH$_2$CH=CH$_2$ | CH$_3$ | CH$_3$ |
| Ia1.342 | or Ib1.342 | Cl | H | OCOcyclopropyl | CH$_3$ | CH$_3$ |
| Ia1.343 | or Ib1.343 | Cl | H | OCOcyclopentyl | CH$_3$ | CH$_3$ |
| Ia1.344 | or Ib1.344 | Cl | H | OCOcyclohexyl | CH$_3$ | CH$_3$ |
| Ia1.345 | or Ib1.345 | Cl | H | OCO(2-tetrahydro-furyl) | CH$_3$ | CH$_3$ |
| Ia1.346 | or Ib1.346 | Cl | H | OCO(2-furyl) | CH$_3$ | CH$_3$ |
| Ia1.347 | or Ib1.347 | Cl | H | OCO(2-thienyl) | CH$_3$ | CH$_3$ |
| Ia1.348 | or Ib1.348 | Cl | H | OCO(3-pyridyl) | CH$_3$ | CH$_3$ |
| Ia1.349 | or Ib1.349 | OCH$_3$ | H | F | CH$_3$ | H |
| Ia1.350 | or Ib1.350 | OCH$_3$ | H | Cl | CH$_3$ | H |
| Ia1.351 | or Ib1.351 | OCH$_3$ | H | Br | CH$_3$ | H |
| Ia1.352 | or Ib1.352 | OCH$_3$ | H | I | CH$_3$ | H |
| Ia1.353 | or Ib1.353 | OCH$_3$ | H | SO$_2$CH$_3$ | CH$_3$ | H |
| Ia1.354 | or Ib1.354 | OCH$_3$ | H | SO$_2$CH$_2$CH$_3$ | CH$_3$ | H |
| Ia1.355 | or Ib1.355 | OCH$_3$ | H | SC$_6$H$_5$ | CH$_3$ | H |
| Ia1.356 | or Ib1.356 | OCH$_3$ | H | S(4-CH$_3$—C$_6$H$_4$) | CH$_3$ | H |
| Ia1.357 | or Ib1.357 | OCH$_3$ | H | S(4-Cl—C$_6$H$_4$) | CH$_3$ | H |
| Ia1.358 | or Ib1.358 | OCH$_3$ | H | SO$_2$C$_6$H$_5$ | CH$_3$ | H |
| Ia1.359 | or Ib1.359 | OCH$_3$ | H | SO$_2$(4-CH$_3$—C$_6$H$_4$) | CH$_3$ | H |
| Ia1.360 | or Ib1.360 | OCH$_3$ | H | SO$_2$(4-Cl—C$_6$H$_4$) | CH$_3$ | H |
| Ia1.361 | or Ib1.361 | OCH$_3$ | H | 1-morpholinyl | CH$_3$ | H |
| Ia1.362 | or Ib1.362 | OCH$_3$ | H | i-pyrrolidinyl | CH$_3$ | H |
| Ia1.363 | or Ib1.363 | OCH$_3$ | H | 1-(1,2,4-triazolyl) | CH$_3$ | H |
| Ia1.364 | or Ib1.364 | OCH$_3$ | H | 1-imidazolyl | CH$_3$ | H |
| Ia1.365 | or Ib1.365 | OCH$_3$ | H | N(OCH$_3$)CH$_3$ | CH$_3$ | H |
| Ia1.366 | or Ib1.366 | OCH$_3$ | H | 2-tetrahydro-isoxazolyl | CH$_3$ | H |
| Ia1.367 | or Ib1.367 | OCH$_3$ | H | N(CH$_3$)N(CH$_3$)$_2$ | CH$_3$ | H |
| Ia1.368 | or Ib1.368 | OCH$_3$ | H | N(CH$_2$CH=CH$_2$)N(CH$_3$)$_2$ | CH$_3$ | H |
| Ia1.369 | or Ib1.369 | OCH$_3$ | H | OPO(OCH$_3$)$_2$ | CH$_3$ | H |
| Ia1.370 | or Ib1.370 | OCH$_3$ | H | OPO(OCH$_2$CH$_3$)$_2$ | CH$_3$ | H |
| Ia1.371 | or Ib1.371 | OCH$_3$ | H | OPO(OC$_6$H$_5$)$_2$ | CH$_3$ | H |

TABLE 1-continued

[Structures Ia1 and Ib1 shown]

| No. | | $R^1$ | $R^3$ | $R^8$ | $R^9$ | $R^{10}$ |
|---|---|---|---|---|---|---|
| Ia1.372 | or Ib1.372 | $OCH_3$ | H | $OPO(CH_3)_2$ | $CH_3$ | H |
| Ia1.373 | or Ib1.373 | $OCH_3$ | H | $OPO(CH_2CH_3)_2$ | $CH_3$ | H |
| Ia1.374 | or Ib1.374 | $OCH_3$ | H | $OPO(C_6H_5)_2$ | $CH_3$ | H |
| Ia1.375 | or Ib1.375 | $OCH_3$ | H | $OPS(OCH_3)_2$ | $CH_3$ | H |
| Ia1.376 | or Ib1.376 | $OCH_3$ | H | $OPS(OCH_2CH_3)_2$ | $CH_3$ | H |
| Ia1.377 | or Ib1.377 | $OCH_3$ | H | $PO(CH_3)_2$ | $CH_3$ | H |
| Ia1.378 | or Ib1.378 | $OCH_3$ | H | $PO(OCH_2CH_3)_2$ | $CH_3$ | H |
| Ia1.379 | or Ib1.379 | $OCH_3$ | H | $PO(C_6H_5)_2$ | $CH_3$ | H |
| Ia1.380 | or Ib1.380 | $OCH_3$ | H | $OCH_2C_6H_5$ | $CH_3$ | H |
| Ia1.381 | or Ib1.381 | $OCH_3$ | H | $OCH_2$(2-furyl) | $CH_3$ | H |
| Ia1.382 | or Ib1.382 | $OCH_3$ | H | $OCH_2$(3-furyl) | $CH_3$ | H |
| Ia1.383 | or Ib1.383 | $OCH_3$ | H | $OCOOCH_3$ | $CH_3$ | H |
| Ia1.384 | or Ib1.384 | $OCH_3$ | H | $OCOOCH_2CH_3$ | $CH_3$ | H |
| Ia1.385 | or Ib1.385 | $OCH_3$ | H | $OCOOCH(CH_3)_2$ | $CH_3$ | H |
| Ia1.386 | or Ib1.386 | $OCH_3$ | H | $OCOOC_6H_5$ | $CH_3$ | H |
| Ia1.387 | or Ib1.387 | $OCH_3$ | H | $OCOOC(CH_3)_3$ | $CH_3$ | H |
| Ia1.388 | or Ib1.388 | $OCH_3$ | H | $OCSOC_6H_5$ | $CH_3$ | H |
| Ia1.389 | or Ib1.389 | $OCH_3$ | H | $OCSN(CH_3)_2$ | $CH_3$ | H |
| Ia1.390 | or Ib1.390 | $OCH_3$ | H | $OCON(CH_3)_2$ | $CH_3$ | H |
| Ia1.391 | or Ib1.391 | $OCH_3$ | H | $OCOSCH_3$ | $CH_3$ | H |
| Ia1.392 | or Ib1.392 | $OCH_3$ | H | $ON(CH_3)_2$ | $CH_3$ | H |
| Ia1.393 | or Ib1.393 | $OCH_3$ | H | O-1-piperidyl | $CH_3$ | H |
| Ia1.394 | or Ib1.394 | $OCH_3$ | H | $OCO(CH_2)_2CH_3$ | $CH_3$ | H |
| Ia1.395 | or Ib1.395 | $OCH_3$ | H | $OCO(CH_2)_6CH_3$ | $CH_3$ | H |
| Ia1.396 | or Ib1.396 | $OCH_3$ | H | $OCO(CH_2)_7CH_3$ | $CH_3$ | H |
| Ia1.397 | or Ib1.397 | $OCH_3$ | H | $OCO(CH_2)_{16}CH_3$ | $CH_3$ | H |
| Ia1.398 | or Ib1.398 | $OCH_3$ | H | $OCO(CH_2)_{14}CH_3$ | $CH_3$ | H |
| Ia1.399 | or Ib1.399 | $OCH_3$ | H | $OCOCH_2CH_2CH=CH_2$ | $CH_3$ | H |
| Ia1.400 | or Ib1.400 | $OCH_3$ | H | OCOcyclopropyl | $CH_3$ | H |
| Ia1.401 | or Ib1.401 | $OCH_3$ | H | OCOcyclopentyl | $CH_3$ | H |
| Ia1.402 | or Ib1.402 | $OCH_3$ | H | OCOcyclohexyl | $CH_3$ | H |
| Ia1.403 | or Ib1.403 | $OCH_3$ | H | OCO(2-tetrahydro-furyl) | $CH_3$ | H |
| Ia1.404 | or Ib1.404 | $OCH_3$ | H | OCO(2-furyl) | $CH_3$ | H |
| Ia1.405 | or Ib1.405 | $OCH_3$ | H | OCO(2-thienyl) | $CH_3$ | H |
| Ia1.406 | or Ib1.406 | $OCH_3$ | H | OCO(3-pyridyl) | $CH_3$ | H |
| Ia1.407 | or Ib1.407 | $OCH_3$ | H | F | $CH_2CH_3$ | H |
| Ia1.408 | or Ib1.408 | $OCH_3$ | H | Cl | $CH_2CH_3$ | H |
| Ia1.409 | or Ib1.409 | $OCH_3$ | H | Br | $CH_2CH_3$ | H |
| Ia1.410 | or Ib1.410 | $OCH_3$ | H | I | $CH_2CH_3$ | H |
| Ia1.411 | or Ib1.411 | $OCH_3$ | H | $SO_2CH_3$ | $CH_2CH_3$ | H |
| Ia1.412 | or Ib1.412 | $OCH_3$ | H | $SO_2CH_2CH_3$ | $CH_2CH_3$ | H |
| Ia1.413 | or Ib1.413 | $OCH_3$ | H | $SC_6H_5$ | $CH_2CH_3$ | H |
| Ia1.414 | or Ib1.414 | $OCH_3$ | H | $S(4-CH_3-C_6H_4)$ | $CH_2CH_3$ | H |
| Ia1.415 | or Ib1.415 | $OCH_3$ | H | $S(4-Cl-C_6H_4)$ | $CH_2CH_3$ | H |
| Ia1.416 | or Ib1.416 | $OCH_3$ | H | $SO_2C_6H_5$ | $CH_2CH_3$ | H |
| Ia1.417 | or Ib1.417 | $OCH_3$ | H | $SO_2(4-CH_3-C_6H_4)$ | $CH_2CH_3$ | H |
| Ia1.418 | or Ib1.418 | $OCH_3$ | H | $SO_2(4-Cl-C_6H_4)$ | $CH_2CH_3$ | H |
| Ia1.419 | or Ib1.419 | $OCH_3$ | H | 4-morpholinyl | $CH_2CH_3$ | H |
| Ia1.420 | or Ib1.420 | $OCH_3$ | H | 1-pyrrolidinyl | $CH_2CH_3$ | H |
| Ia1.421 | or Ib1.421 | $OCH_3$ | H | 1-(1,2,4-triazolyl) | $CH_2CH_3$ | H |
| Ia1.422 | or Ib1.422 | $OCH_3$ | H | 1-imidazolyl | $CH_2CH_3$ | H |
| Ia1.423 | or Ib1.423 | $OCH_3$ | H | $N(OCH_3)CH_3$ | $CH_2CH_3$ | H |
| Ia1.424 | or Ib1.424 | $OCH_3$ | H | 2-tetrahydro-isoxazolyl | $CH_2CH_3$ | H |
| Ia1.425 | or Ib1.425 | $OCH_3$ | H | $N(CH_3)N(CH_3)_2$ | $CH_2CH_3$ | H |
| Ia1.426 | or Ib1.426 | $OCH_3$ | H | $N(CH_2CH=CH_2)N(CH_3)_2$ | $CH_2CH_3$ | H |
| Ia1.427 | or Ib1.427 | $OCH_3$ | H | $OPO(OCH_3)_2$ | $CH_2CH_3$ | H |
| Ia1.428 | or Ib1.428 | $OCH_3$ | H | $OPO(OCH_2CH_3)_2$ | $CH_2CH_3$ | H |
| Ia1.429 | or Ib1.429 | $OCH_3$ | H | $OPO(OC_6H_5)_2$ | $CH_2CH_3$ | H |
| Ia1.430 | or Ib1.430 | $OCH_3$ | H | $OPO(CH_3)_2$ | $CH_2CH_3$ | H |
| Ia1.431 | or Ib1.431 | $OCH_3$ | H | $OPO(CH_2CH_3)_2$ | $CH_2CH_3$ | H |
| Ia1.432 | or Ib1.432 | $OCH_3$ | H | $OPO(C_6H_5)_2$ | $CH_2CH_3$ | H |
| Ia1.433 | or Ib1.433 | $OCH_3$ | H | $OPS(OCH_3)_2$ | $CH_2CH_3$ | H |

TABLE 1-continued

| No. | | $R^1$ | $R^3$ | $R^8$ | $R^9$ | $R^{10}$ |
|---|---|---|---|---|---|---|
| Ia1.434 | or Ib1.434 | OCH$_3$ | H | OPS(OCH$_2$CH$_3$)$_2$ | CH$_2$CH$_3$ | H |
| Ia1.435 | or Ib1.435 | OCH$_3$ | H | PO(OCH$_3$)$_2$ | CH$_2$CH$_3$ | H |
| Ia1.436 | or Ib1.436 | OCH$_3$ | H | PO(OCH$_2$CH$_3$)$_2$ | CH$_2$CH$_3$ | H |
| Ia1.437 | or Ib1.437 | OCH$_3$ | H | PO(C$_6$H$_5$)$_2$ | CH$_2$CH$_3$ | H |
| Ia1.438 | or Ib1.438 | OCH$_3$ | H | OCH$_2$C$_6$H$_5$ | CH$_2$CH$_3$ | H |
| Ia1.439 | or Ib1.439 | OCH$_3$ | H | OCH$_2$(2-furyl) | CH$_2$CH$_3$ | H |
| Ia1.440 | or Ib1.440 | OCH$_3$ | H | OCH$_2$(3-furyl) | CH$_2$CH$_3$ | H |
| Ia1.441 | or Ib1.441 | OCH$_3$ | H | OCOOCH$_3$ | CH$_2$CH$_3$ | H |
| Ia1.442 | or Ib1.442 | OCH$_3$ | H | OCOOCH$_2$CH$_3$ | CH$_2$CH$_3$ | H |
| Ia1.443 | or Ib1.443 | OCH$_3$ | H | OCOOCH(CH$_3$)$_2$ | CH$_2$CH$_3$ | H |
| Ia1.444 | or Ib1.444 | OCH$_3$ | H | OCOOC$_6$H$_5$ | CH$_2$CH$_3$ | H |
| Ia1.445 | or Ib1.445 | OCH$_3$ | H | OCOOC(CH$_3$)$_3$ | CH$_2$CH$_3$ | H |
| Ia1.446 | or Ib1.446 | OCH$_3$ | H | OCSOC$_6$H$_5$ | CH$_2$CH$_3$ | H |
| Ia1.447 | or Ib1.447 | OCH$_3$ | H | OCSN(CH$_3$)$_2$ | CH$_2$CH$_3$ | H |
| Ia1.448 | or Ib1.448 | OCH$_3$ | H | OCON(CH$_3$)$_2$ | CH$_2$CH$_3$ | H |
| Ia1.449 | or Ib1.449 | OCH$_3$ | H | OCOSCH$_3$ | CH$_2$CH$_3$ | H |
| Ia1.450 | or Ib1.450 | OCH$_3$ | H | ON(CH$_3$)$_2$ | CH$_2$CH$_3$ | H |
| Ia1.451 | or Ib1.451 | OCH$_3$ | H | O-1-piperidyl | CH$_2$CH$_3$ | H |
| Ia1.452 | or Ib1.452 | OCH$_3$ | H | OCO(CH$_2$)$_2$CH$_3$ | CH$_2$CH$_3$ | H |
| Ia1.453 | or Ib1.453 | OCH$_3$ | H | OCO(CH$_2$)$_6$CH$_3$ | CH$_2$CH$_3$ | H |
| Ia1.454 | or Ib1.454 | OCH$_3$ | H | OCO(CH$_2$)$_7$CH$_3$ | CH$_2$CH$_3$ | H |
| Ia1.455 | or Ib1.455 | OCH$_3$ | H | OCO(CH$_2$)$_{16}$CH$_3$ | CH$_2$CH$_3$ | H |
| Ia1.456 | or Ib1.456 | OCH$_3$ | H | OCO(CH$_2$)$_{14}$CH$_3$ | CH$_2$CH$_3$ | H |
| Ia1.457 | or Ib1.457 | OCH$_3$ | H | OCOCH$_2$CH$_2$CH=CH$_2$ | CH$_2$CH$_3$ | H |
| Ia1.458 | or Ib1.458 | OCH$_3$ | H | OCOcyclopropyl | CH$_2$CH$_3$ | H |
| Ia1.459 | or Ib1.459 | OCH$_3$ | H | OCOcyclopentyl | CH$_2$CH$_3$ | H |
| Ia1.460 | or Ib1.460 | OCH$_3$ | H | OCOcyclohexyl | CH$_2$CH$_3$ | H |
| Ia1.461 | or Ib1.461 | OCH$_3$ | H | OCO(2-tetrahydro-furyl) | CH$_2$CH$_3$ | H |
| Ia1.462 | or Ib1.462 | OCH$_3$ | H | OCO(2-furyl) | CH$_2$CH$_3$ | H |
| Ia1.463 | or Ib1.463 | OCH$_3$ | H | OCO(2-thienyl) | CH$_2$CH$_3$ | H |
| Ia1.464 | or Ib1.464 | OCH$_3$ | H | OCO(3-pyridyl) | CH$_2$CH$_3$ | H |
| Ia1.465 | or Ib1.465 | OCH$_3$ | H | F | CH$_3$ | CH$_3$ |
| Ia1.466 | or Ib1.466 | OCH$_3$ | H | Cl | CH$_3$ | CH$_3$ |
| Ia1.467 | or Ib1.467 | OCH$_3$ | H | Br | CH$_3$ | CH$_3$ |
| Ia1.468 | or Ib1.468 | OCH$_3$ | H | I | CH$_3$ | CH$_3$ |
| Ia1.469 | or Ib1.469 | OCH$_3$ | H | SO$_2$CH$_3$ | CH$_3$ | CH$_3$ |
| Ia1.470 | or Ib1.470 | OCH$_3$ | H | SO$_2$CH$_2$CH$_3$ | CH$_3$ | CH$_3$ |
| Ia1.471 | or Ib1.471 | OCH$_3$ | H | SC$_6$H$_5$ | CH$_3$ | CH$_3$ |
| Ia1.472 | or Ib1.472 | OCH$_3$ | H | S(4-CH$_3$—C$_6$H$_4$) | CH$_3$ | CH$_3$ |
| Ia1.473 | or Ib1.473 | OCH$_3$ | H | S(4-Cl—C$_6$H$_4$) | CH$_3$ | CH$_3$ |
| Ia1.474 | or Ib1.474 | OCH$_3$ | H | SO$_2$C$_6$H$_5$ | CH$_3$ | CH$_3$ |
| Ia1.475 | or Ib1.475 | OCH$_3$ | H | SO$_2$(4-CH$_3$—C$_6$H$_4$) | CH$_3$ | CH$_3$ |
| Ia1.476 | or Ib1.476 | OCH$_3$ | H | SO$_2$(4-Cl—C$_6$H$_4$) | CH$_3$ | CH$_3$ |
| Ia1.477 | or Ib1.477 | OCH$_3$ | H | 1-morpholinyl | CH$_3$ | CH$_3$ |
| Ia1.478 | or Ib1.478 | OCH$_3$ | H | 1-pyrrolidinyl | CH$_3$ | CH$_3$ |
| Ia1.479 | or Ib1.479 | OCH$_3$ | H | 1-(1,2,4-triazolyl) | CH$_3$ | CH$_3$ |
| Ia1.480 | or Ib1.480 | OCH$_3$ | H | 1-imidazolyl | CH$_3$ | CH$_3$ |
| Ia1.481 | or Ib1.481 | OCH$_3$ | H | N(OCH$_3$)CH$_3$ | CH$_3$ | CH$_3$ |
| Ia1.482 | or Ib1.482 | OCH$_3$ | H | 2-tetrahydro-isoxazolyl | CH$_3$ | CH$_3$ |
| Ia1.483 | or Ib1.483 | OCH$_3$ | H | N(CH$_3$)N(CH$_3$)$_2$ | CH$_3$ | CH$_3$ |
| Ia1.484 | or Ib1.484 | OCH$_3$ | H | N(CH$_2$CH=CH$_2$)N(CH$_3$)$_2$ | CH$_3$ | CH$_3$ |
| Ia1.485 | or Ib1.485 | OCH$_3$ | H | OPO(OCH$_3$)$_2$ | CH$_3$ | CH$_3$ |
| Ia1.486 | or Ib1.486 | OCH$_3$ | H | OPO(OCH$_2$CH$_3$)$_2$ | CH$_3$ | CH$_3$ |
| Ia1.487 | or Ib1.487 | OCH$_3$ | H | OPO(OC$_6$H$_5$)$_2$ | CH$_3$ | CH$_3$ |
| Ia1.488 | or Ib1.488 | OCH$_3$ | H | OPO(CH$_3$)$_2$ | CH$_3$ | CH$_3$ |
| Ia1.489 | or Ib1.489 | OCH$_3$ | H | OPO(CH$_2$CH$_3$)$_2$ | CH$_3$ | CH$_3$ |
| Ia1.490 | or Ib1.490 | OCH$_3$ | H | OPO(C$_6$H$_5$)$_2$ | CH$_3$ | CH$_3$ |
| Ia1.491 | or Ib1.491 | OCH$_3$ | H | OPS(OCH$_3$)$_2$ | CH$_3$ | CH$_3$ |
| Ia1.492 | or Ib1.492 | OCH$_3$ | H | OPS(OCH$_2$CH$_3$)$_2$ | CH$_3$ | CH$_3$ |
| Ia1.493 | or Ib1.493 | OCH$_3$ | H | PO(OCH$_3$)$_2$ | CH$_3$ | CH$_3$ |
| Ia1.494 | or Ib1.494 | OCH$_3$ | H | PO(OCH$_2$CH$_3$)$_2$ | CH$_3$ | CH$_3$ |
| Ia1.495 | or Ib1.495 | OCH$_3$ | H | PO(C$_6$H$_5$)$_2$ | CH$_3$ | CH$_3$ |

TABLE 1-continued

| No. | R¹ | R³ | R⁸ | R⁹ | R¹⁰ |
|---|---|---|---|---|---|
| Ia1.496 or Ib1.496 | OCH₃ | H | OCH₂C₆H₅ | CH₃ | CH₃ |
| Ia1.497 or Ib1.497 | OCH₃ | H | OCH₂(2-furyl) | CH₃ | CH₃ |
| Ia1.498 or Ib1.498 | OCH₃ | H | OCH₂(3-furyl) | CH₃ | CH₃ |
| Ia1.499 or Ib1.499 | OCH₃ | H | OCOOCH₃ | CH₃ | CH₃ |
| Ia1.500 or Ib1.500 | OCH₃ | H | OCOOCH₂CH₃ | CH₃ | CH₃ |
| Ia1.501 or Ib1.501 | OCH₃ | H | OCOOCH(CH₃)₂ | CH₃ | CH₃ |
| Ia1.502 or Ib1.502 | OCH₃ | H | OCOOC₆H₅ | CH₃ | CH₃ |
| Ia1.503 or Ib1.503 | OCH₃ | H | OCOOC(CH₃)₃ | CH₃ | CH₃ |
| Ia1.504 or Ib1.504 | OCH₃ | H | OCSOC₆H₅ | CH₃ | CH₃ |
| Ia1.505 or Ib1.505 | OCH₃ | H | OCSN(CH₃)₂ | CH₃ | CR3 |
| Ia1.506 or Ib1.506 | OCH₃ | H | OCON(CH₃)₂ | CH₃ | CH₃ |
| Ia1.507 or Ib1.507 | OCH₃ | H | OCOSCH₃ | CH₃ | CH₃ |
| Ia1.508 or Ib1.508 | OCH₃ | H | ON(CH₃)₂ | CH₃ | CH₃ |
| Ia1.509 or Ib1.509 | OCH₃ | H | O-1-piperidyl | CH₃ | CH₃ |
| Ia1.510 or Ib1.510 | OCH₃ | H | OCO(CH)₂CH₃ | CH₃ | CH₃ |
| Ia1.511 or Ib1.511 | OCH₃ | H | OCO(CH)₆CH₃ | CH₃ | CH₃ |
| Ia1.512 or Ib1.512 | OCH₃ | H | OCO(CH)₇CH₃ | CH₃ | CH₃ |
| Ia1.513 or Ib1.513 | OCH₃ | H | OCO(CH)₁₆CH₃ | CH₃ | CH₃ |
| Ia1.514 or Ib1.514 | OCH₃ | H | OCO(CH)₁₄CH₃ | CH₃ | CH₃ |
| Ia1.515 or Ib1.515 | OCH₃ | H | OCOCH₂CH₂CH=CH₂ | CH₃ | CH₃ |
| Ia1.516 or Ib1.516 | OCH₃ | H | OCOcyclopropyl | CH₃ | CH₃ |
| Ia1.517 or Ib1.517 | OCH₃ | H | OCOcyclopentyl | CH₃ | CH₃ |
| Ia1.518 or Ib1.518 | OCH₃ | H | OCOcyclohexyl | CH₃ | CH₃ |
| Ia1.519 or Ib1.519 | OCH₃ | H | OCO(2-tetrahydro-furyl) | CH₃ | CH₃ |
| Ia1.520 or Ib1.520 | OCH₃ | H | OCO(2-furyl) | CH₃ | CH₃ |
| Ia1.521 or Ib1.521 | OCH₃ | H | OCO(2-thienyl) | CH₃ | CH₃ |
| Ia1.522 or Ib1.522 | OCH₃ | H | OCO(3-pyridyl) | CH₃ | CH₃ |

Furthermore, extraordinary preference is given to the following pyrazolyldioxothiochromanoyl derivatives of the formula I:

The compounds of the formulae Ia2 and Ib2, in particular the compounds Ia2.1 to Ia2.522 and the compounds Ib2.1 to Ib2.522, which differ from the compounds Ia1.1 to Ia1.522 and Ib1.1 to Ib1.522 in that X is CH(CH₃).

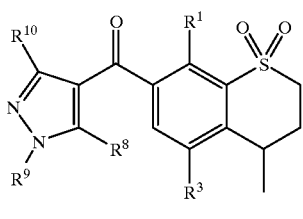

Ia2

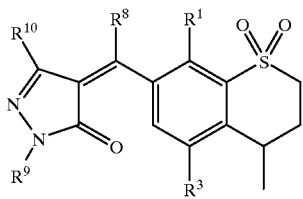

Ib2

The compounds of the formulae Ia3 and Ib3, in particular the compounds Ia3.1 to Ia3.522 and the compounds Ib3.1 to Ib3.522, which differ from the compounds Ia1.1 to Ia1.522 and Ib1.1 to Ib1.522 in that X is CH(OCH₃).

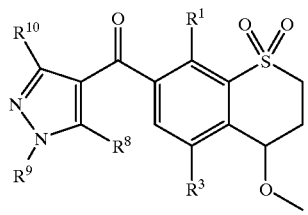

Ia3

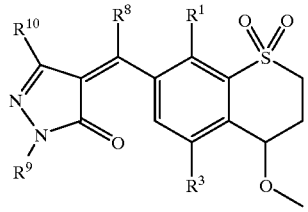

Ib3

The compounds of the formulae Ia4 and Ib4, in particular the compounds Ia4.1 to Ia4.522 and the compounds Ib4.1 to Ib4.522, which differ from the compounds Ia1.1 to Ia1.522 and Ib1.1 to Ib1.522 in that X is C(CH₃)(OCH₃).

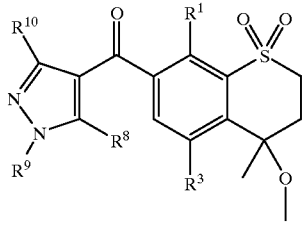
Ia4

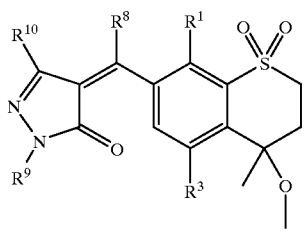
Ib4

The compounds of the formulae Ia5 and Ib5, in particular the compounds Ia5.1 to Ia5.522 and the compounds Ib5.1 to Ib5.522, which differ from the compounds Ia1.1 to Ia1.522 and Ib1.1 to Ib1.522 in that X is C=O.

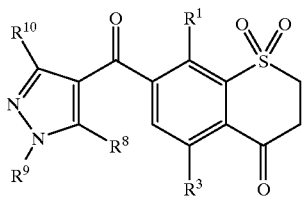
Ia5

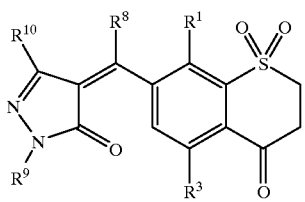
Ib5

The compounds of the formulae Ia6 and Ib6, in particular the compounds Ia6.1 to Ia6.522 and the compounds Ib6.1 to Ib6.522, which differ from the compounds Ia1.1 to Ia1.522 and Ib1.1 to Ib1.522 in that X is C=NOCH₃.

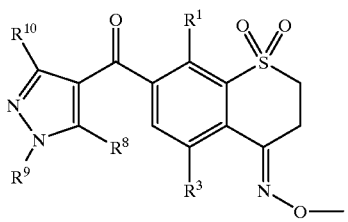
Ia6

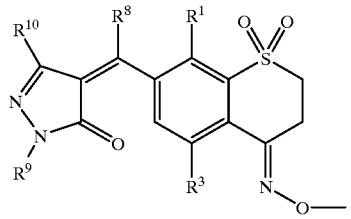
Ib6

The compounds of the formulae Ia7 and Ib7, in particular the compounds Ia7.1 to Ia7.522 and the compounds Ib7.1 to Ib7.522, which differ from the compounds Ia1.1 to Ia1.522 and Ib1.1 to Ib1.522 in that X is C(OCH₃)₂.

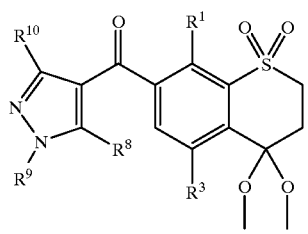
Ia7

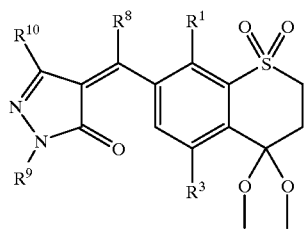
Ib7

The compounds of the formulae Ia8 and Ib8, in particular the compounds Ia8.1 to Ia8.522 and the compounds Ib8.1 to Ib8.522, which differ from the compounds Ia1.1 to Ia1.522 and Ib1.1 to Ib1.522 in that X is S(=O)₂

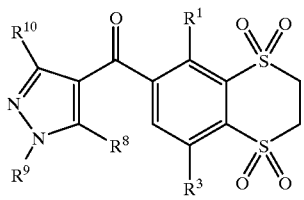
Ia8

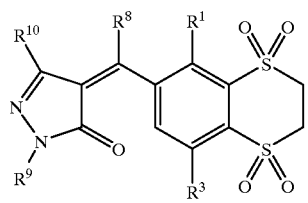
Ib8

Extraordinary preference is furthermore given to the compounds Ia, in particular the compounds Ia1 to Ia8, and to the particular embodiments mentioned.

The pyrazolyldioxothiochromanoyl derivatives of the formula I can be obtained by various routes, for example by the following processes:

A. Preparation of compounds of the formula I where $R^8$=halogen by reaction of pyrazolone derivatives of the formula III with halogenating agents:

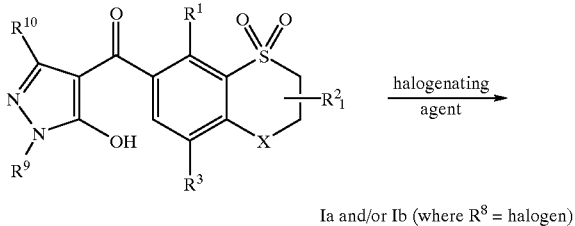

Ia and/or Ib (where $R^8$ = halogen)

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylalmonium chloride, oxylyl bromide, phosphorus oxybromide, etc.

The starting materials are generally employed in equimolar amounts. However, it may also be advantageous to employ an excess of one or other component.

Suitable solvents are, for example, chlorinated hydrocarbons, such as methylene chloride or 1,2-dichloroethane, aromatic hydrocarbons, for example toluene, xylene or chlorobenzene, polar aprotic solvents, such as acetonitrile, dimethylformamide or dimethyl sulfoxide, or mixtures of these. The reaction can also be carried out without solvent.

The reaction temperature is generally in the range of from 0° C. to the boiling point of the reaction mixture.

Work-up to afford the product can be carried in the manner known per se.

B. Preparation of compounds of the formula I where $R^8$=$OR^{11}$, $OPOR^{12}R^{13}$ or $OPSR^{12}R^{13}$ by reaction of pyrazolone derivatives of the formula III with alkylating or phosphonylating agents IVα, IVβ or IVγ.

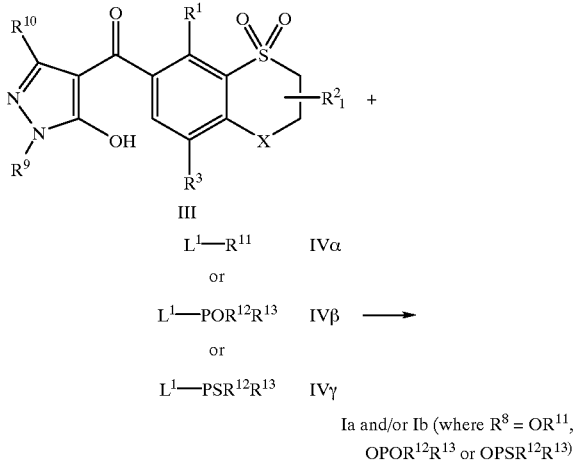

Ia and/or Ib (where $R^8$ = $OR^{11}$, $OPOR^{12}R^{13}$ or $OPSR^{12}R^{13}$)

$L^1$ represents a nucleophilically replaceable leaving group, such as halogen, for example chlorine or bromine, hetaryl, for example imidazolyl, carboxylate, for example acetate, or sulfonate, for example mesylate or triflate, etc.

The compounds of the formula IVα, IVβ or IVγ can be employed directly, such as, for example, in the case of the carbonyl halides, or they can be generated in situ, for example activated carboxylic acids (using carboxylic acid and dicyclohexylcarbodiimide, etc.).

The starting materials are generally employed in equimolar amounts. However, it may also be advantageous to employ an excess of one or other component.

If appropriate, it may be advantageous to carry out the reactions in the presence of a base. The starting materials and the base are advantageously employed in equimolar amounts. An excess of base, for example 1.5 to 3 molar equivalents, may be advantageous in certain cases.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

The reaction temperature is generally in the range of from 0° C. to the boiling point of the reaction mixture.

Work-up to afford the product can be carried in the manner known per se.

C. Preparation of compounds of the formula I where $R^8$=$OR^{11}$, $SR^{11}$, $POR^{12}R^{13}$, $NR^{14}R^{15}$, $ONR^{15}R^{15}$, N-bonded heterocyclyl or O—(N-bonded heterocyclyl) by reaction of compounds of the formula I where $R^8$=halogen (Iα) with compounds of the formula Vα, Vβ, Vγ, Vδ, Vε, Vη or Vθ, if appropriate in the presence of a base or with prior formation of salt.

| Ia and/or Ib (where $R^8$ = halogen) | + | $HOR^{11}$ or $HSR^{11}$ or $HPOR^{12}R^{13}$ or $HNR^{14}R^{15}$ or $HONR^{15}R^{15}$ or H(N-bonded heterocyclyl) or HO(N-bonded heterocyclyl) | Vα Vβ → Vγ Vδ Vε Vη Vθ | Ia and/or Ib (where $R^8$ = $OR^{11}$, $SR^{11}$, $POR^{12}R^{13}$, $NR^{14}R^{15}$, $ONR^{15}R^{15}$, N-bonded heterocyclyl or O-(N-bonded heterocyclyl)) |

The starting materials are generally employed in equimolar amounts. However, it may also be advantageous to employ an excess of one or other component.

If appropriate, it may be advantageous to carry out the reactions in the presence of a base. The starting materials and the base are advantageously employed in equimolar amounts. An excess of base, for example 1.5 to 3 molar equivalents, based on Ia and/or Ib (where $R^8$=halogen) or III may be advantageous in certain cases.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using sodium hydride or potassium tert-butoxide.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or mixtures of these.

The reaction temperature is generally in the range of from 0° C. to the boiling point of the reaction mixture.

Work-up to afford the product can be carried in the manner known per se.

D. Preparation of compounds of the formula I where $R^8$=$SOR^{12}$, $SO_2R^{12}$ by reaction of compounds of the formula I where $R^8$=$SR^{12}$ (Iβ) with an oxidizing agent.

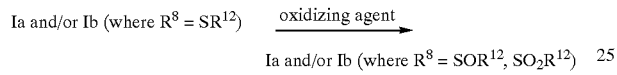

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

The reaction temperature is generally in the range of from 0° C. to the boiling point of the reaction mixture.

Work-up to afford the product can be carried in the manner known per se.

E. Preparation of compounds of the formula I where $R^7$=IIa by reaction of a metallated pyrazole derivative of the formula VI with a dioxothiochromancarboxylic acid derivative of the formula VII:

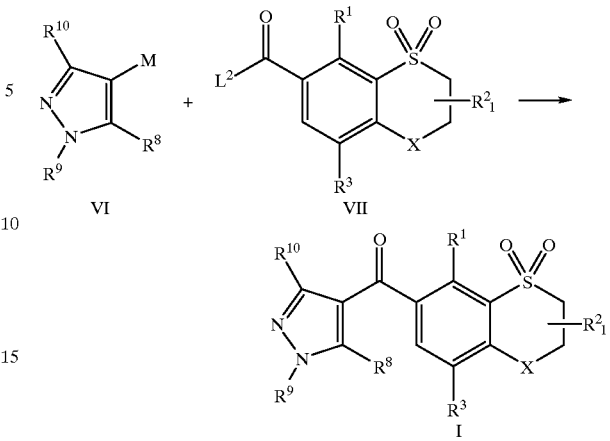

M is a metal, in particular an alkali metal, such as lithium or sodium, an alkaline earth metal, such as, for example, magnesium, or a transition metal, such as palladium, nickel, etc., and $L^2$ is a nucleophilically replaceable leaving group, such as halogen, for example chlorine or bromine, alkyl sulfonate, such as mesylate, haloalkyl sulfonate, such as triflate, or cyanide.

The reaction is generally carried out at temperatures of from −100° C. to the reflux temperature of the reaction mixture. Suitable solvents are inert aprotic solvents, such as ethers, for example diethyl ether, tetrahydrofuran. The compounds of the formula VII are generally employed in excess, but it may also be advantageous to employ them in equimolar amounts or in excess. Work-up is carried out to obtain the product.

Depending on the reaction conditions, the compounds Ia, Ib or mixtures of these can be formed. The latter can be separated by classic separation methods, such as, for example, crystallization, chromatography, etc.

The pyrazolone derivatives of the formula III are known or can be prepared by processes known per se (for example DE 19 532 312). An example is given by the reaction of pyrazolones of the formula VIII with an activated benzoic acid VIIa or a benzoic acid VIIb, which is preferably activated in situ, to give the acylation product, followed by rearrangement.

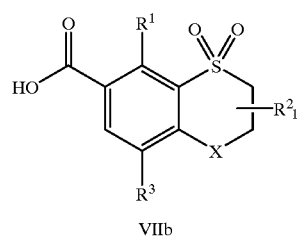

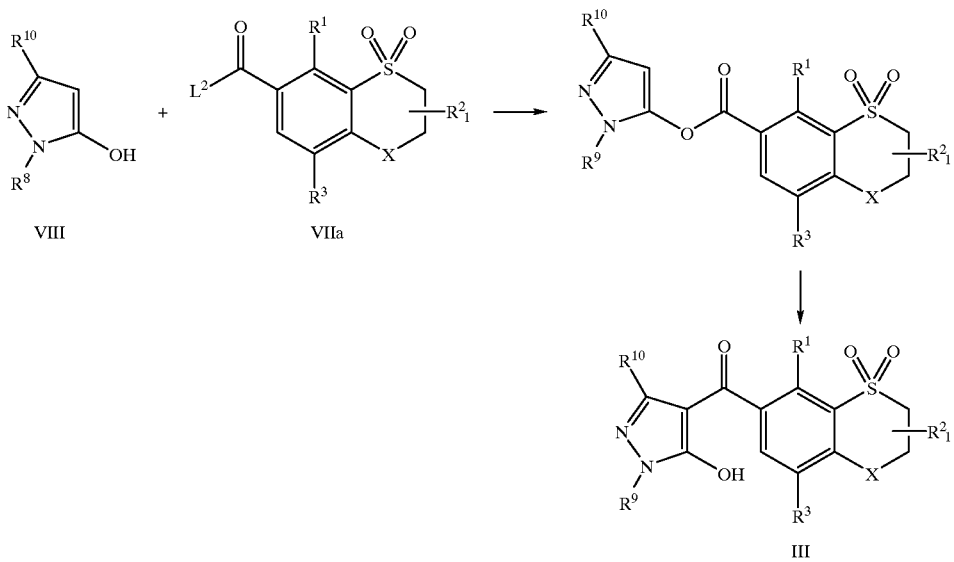

$L^2$ is a nucleophilically replaceable leaving group, such as halogen, for example bromine or chlorine, hetaryl, for example, imidazolyl or pyridyl, carboxylate, for example acetate or trifluoroacetate, etc.

The activated benzoic acid VIIa can be employed directly, such as in the case of the benzoyl halides, or be generated in situ, for example using dicyclohexylcarbodiimide, triphenylphosphine/azodicarboxylic esters, 2-pyridine disulfide/triphenylphosphine, carbonyldiimidazole, etc.

If appropriate, it may be advantageous to carry out the acylation reaction in the presence of a base. The reactants and the auxiliary base are advantageously employed in equimolar amounts. A slight excess of the auxiliary base, for example from 1.2 to 1.5 molar equivalents, based on VII, may be advantageous in certain cases.

Suitable auxiliary bases are tertiary alkylamines, pyridine or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters such as ethyl acetate, or mixtures of these.

If the activated carboxylic acid component used is a benzoyl halide, it may be advantageous to cool the reaction mixture to 0–10° C. when adding this reaction partner. The mixture is subsequently stirred at 20–100° C., preferably at 25–50° C., until the reaction is complete. Work-up is carried out in a customary manner, for example, the reaction mixture is poured into water and the product of value is extracted. Solvents which are suitable for this operation are in particular methylene chloride, diethyl ether and ethyl acetate. The organic phase is dried and the solvent is removed, and the crude ester can then be employed for the rearrangement without any further purification.

The rearrangement of the esters to the compounds of the formula III is advantageously carried out at temperatures of from 20 to 100° C. in a solvent and in the presence of a base and, if appropriate, using a cyano compound as catalyst.

Suitable solvents are, for example, acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, aromatic amines such as pyridine, or alkali metal carbonates, such as sodium carbonate or potassium carbonate, which are preferably employed in equimolar amounts or in up to four-fold excess, based on the ester. Preference is given to using triethylamine or alkali metal carbonate, preferably in twice the equimolar amount, based on the ester.

Suitable cyano compounds are inorganic cyanides, such as sodium cyanide or potassium cyanide, and organic cyano compounds, such as acetone cyanohydrin or trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent based on the ester.

Work-up can be carried out in a manner known per se. For example, the reaction mixture is acidified with dilute mineral acid, such as 5% strength hydrochloric acid or sulfuric acid, and extracted with an organic solvent, for example methylene chloride or ethyl acetate. The organic extract may be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, dried and concentrated.

The benzoyl halides of the formula VIIa (where $L^2$=Cl, Br) can be prepared in a manner known per se by reaction of the benzoic acids of the formula VIIb with halogenating agents such as thionyl chloride, thionyl bromide, phosgene, diphosgene, triphosgene, oxalyl chloride, oxalyl bromide.

The benzoic acids of the formula VIIb can be prepared in a known manner from the corresponding esters by acidic or basic hydrolysis.

The metallated pyrazole derivatives of the formula VI can be prepared in a manner known per se by reaction of pyrazoles which are halogenated in the 4-position, using metals such as lithium, sodium, magnesium, etc., or using organometallic compounds, such as, for example, butyl-lithium. However, it is also possible to metallate pyrazoles which are linked in the 4-position with hydrogen directly, for example using the abovementioned metals or organometallic compounds. The reactions are generally carried out in an inert aprotic solvent, preferably in ethers, such as diethyl ether, tetrahydrofuran, etc. The reaction temperature is in the range from –100° C. to the boiling point of the reaction mixture. The compounds of the formula VI are generally directly reacted further or generated in situ.

PREPARATION EXAMPLES

5-Chloro-1-ethyl-4-(4,4,8-trimethyl-1,1-dioxothiochroman-7-yl)-carbonylpyrazole (Compound 2.1)

Step a)

Methyl 3-(3-methyl-2-butenylthio)-2-methylbenzoate 37.9 g (0.275 mol) of potassium carbonate and 43.5 g (0.275 mol) of 3-methyl-2-butenyl bromide were added dropwise to 50 g (0.275 mol) of methyl 3-thio-2-methylbenzoate in 250 ml of acetone, and the mixture was stirred at room temperature for 10 hours. The solvent was distilled off, the residue was taken up in water/ethyl acetate and the organic phase was dried, filtered off and concentrated.

Yield: 67.9 g (98.9%) of a yellow oil.

$^1$H-NMR (CDCl$_3$, δ in ppm): 7.63 (d,1H); 7.41 (d,1H); 7.16 (t,1H); 5.25 (m,1H); 3.90 (s,3H), 3.49 (d,2H); 2.60 (s,3H); 1.70 (s,3H); 1.56 (s,3H).

Step b)

Methyl 4,4,8-trimethylthiochroman-7-carboxylate 67.9 g (0.27 mol) of methyl 3-(3-methyl-2-butenylthio)-2-methylbenzoate were dissolved in 600 ml of methylene chloride and, at −5 to 0° C., 206.4 g (1.09 mol) of titanium tetrachloride in 600 ml of methylene chloride were added dropwise, and the mixture was stirred at 0° C. for three hours. The mixture was subsequently stirred into 1.5 kg of ice and 500 ml of saturated ammonium chloride solution, the organic phase was separated off and dried and the solvent was removed. This gave 62.9 g of an orange oil which was directly used further. To characterize the product, a sample was chromatographed over silica gel (mobile phase: cyclohexane/ethyl acetate=10/1).

Melting point: 63° C.

Step c)

4,4,8-Trimethylthiochroman-7-carboxylic acid 62.9 g of methyl 4,4,8-trimethylthiochroman-7-carboxylate were initially charged in 600 ml of a 1:1 mixture of water/methanol, and 15.1 g (0.377 mol) of sodium hydroxide were added. The solution was then heated under reflux for three hours, the organic solvent was removed, 200 ml of water were added and the mixture was made acidic using conc. hydrochloric acid with cooling. The precipitate was filtered off with suction, washed with water and dried.

Yield: 57.2 g

Melting point: 212° C.

Step d)

4,4,8-Trimethyl-1,1-dioxothiochroman-7-carboxylic acid 57.2 g (0.24 mol) of 4,4,8-trimethylthiochroman-7-carboxylic acid were dissolved in 500 ml of acetic acid, and a spatula tip of sodium tungstate was added. At 50 to 60° C., 60.4 g (0.53 mol) of 30% strength hydrogen peroxide were added dropwise, the mixture was stirred at 50° C. for three hours and stirred into ice-water, and the precipitated white needles were filtered off, washed with water and dried.

Yield: 47.2 g (72.7%)

Melting point: 280° C. (decomposition)

Step e)

4,4,8-Trimethyl-1,1-dioxothiochroman-7-carbonyl chloride 20.0 g (0.075 mol) of 4,4,8-trimethyl-1,1-dioxothiochroman-7-carboxylic acid were dissolved in 200 ml of toluene and three drops of dimethylformamide and 10.7 g (0.09 mol) of thionyl chloride were added. After three hours of heating under reflux, the solvent was removed and the colorless oil that remained (yield 21.3 g) was directly used further.

Step f)

5-Chloro-1-ethyl-4-(4,4,8-trimethyl-1,1-dioxothiochroman-7-yl)-carbonylpyrazole (Compound 2.1)

Under an atmosphere of protective gas and at 20 to 25° C., 2.6 ml (4.11 mmol) of n-butyllithium in hexane (1.6 molar) were rapidly added dropwise to 0.86 g (4.11 mmol) of 4-bromo-5-chloro-1-ethylpyrazole in 30 ml of diethyl ether. The mixture was stirred at room temperature for 15 minutes and the resulting suspension was then, at −70° C., added dropwise to a solution of 2.2 g (8.21 mmol) of 4,4,8-trimethyl-1,1-dioxothiochroman-7-carbonyl chloride in 30 ml of diethyl ether. The reaction mixture was subsequently warmed to room temperature and mixed with 11 ml of methanol and 26 ml of 2N aqueous sodium hydroxide solution. The organic phase was then separated off, dried and concentrated and the residue was chromatographed over silica gel (mobile phase: ethyl acetate/cyclohexane=3/2).

Yield: 0.17 g

Melting point: 131–133° C.

1-Ethyl-4-(8-methyl-2,3-dihydro-1,1,4,4-tetraoxobenz[1,4]dithiin-7-ylcarbonyl)-5-propylcarbonyloxypyrazole (Compound 2.5)

Step a)

Methyl 3-(2-bromoethylthio)-2-methylbenzoate 30.3 g (0.22 mol) of potassium carbonate were added to 40.0 g (0.22 mol) of methyl 3-thio-2-methylbenzoate in 500 ml of acetone, and 82.6 g (0.22 mol) of 1,2-dibromoethane were added dropwise. After 10 hours of stirring at room temperature, the solvent was distilled off, the residue was taken up in water/ethyl acetate and the organic phase was dried and concentrated. The oil that remained was chromatographed over silica gel using ethyl acetate/cyclohexane=1/10.

Yield: 42.7 g (67.2%) of colorless crystals.

$^1$H-NMR (CDCl$_3$, δ in ppm): 7.68 (d,1H); 7.51 (d,1H); 7.20 (t,1H); 3.90 (s,3H), 3.41 (m,2H); 3.25 (m,2H); 2.62 (s,3H).

Step b)

Methyl 3-(2-methylsulfonylthioethylthio)-2-methylbenzoate 33.2 g (0.22 mol) of potassium methylsulfonylthiolate were added to 42.7 g (0.148 mol) of methyl 3-(2-bromoethylthio)-2-methyl-benzoate in 400 ml of ethanol, and the mixture was heated under reflux for 5 hours. The solvent was removed and the residue was then taken up in water/ethyl acetate, dried and concentrated. The oil that remained was chromatographed over silica gel using ethyl acetate/cyclohexane=1/4.

Yield: 33.2 g (67.2%) of a yellow oil.

Melting point: 55° C.

Step c)

Methyl 8-methyl-2,3-dihydrobenz[1,4]dithiin-7-carboxylate 49.2 g (0.154 mol) of methyl 3-(2-methylsulfonylthio-ethylthio)-2-methylbenzoate were dissolved in 500 ml of methylene chloride, 80.2 g (0.308 mol) of tin tetrachloride were added and the mixture was heated under reflux for three hours and stirred at room temperature for another ten hours. The mixture was then washed with water and saturated sodium bicarbonate solution and the organic phase was separated off, dried and concentrated. The oil that remained was chromatographed over silica gel using ethyl acetate/cyclohexane=1/10.

Yield: 17.1 g (46.3%) of a colorless oil

Melting point: 57° C.

Step d)

8-Methyl-2,3-dihydrobenz[1,4]dithiin-7-carboxylic acid 9.6 g (0.04 mol) of methyl 8-methyl-2,3-dihydrobenz[1,4]dithiin-7-carboxylate were initially charged in 100 ml of a 1:1 mixture of water/methanol and 2.4 g (0.06 mol) of sodium hydroxide were added. The solution was heated under reflux for two hours, then the organic solvent was distilled off, 200 ml of water were added and the mixture was acidified with cooling using conc. hydrochloric acid. The precipitate was filtered off with suction, washed with water and dried.

Yield: 8.1 g (89.6%) of colorless crystals

Melting point: 175° C.

Step e)

8-Methyl-2,3-dihydro-1,1,4,4-tetraoxobenz[1,4]dithiin-7-carboxylic acid 19.4 g (0.086 mol) of 8-methyl-2,3-dihydrobenz[1,4]dithiin-7-carboxylic acid were dissolved in 200 ml of acetic acid, and a spatula tip of sodium tungstate was added. At 50–60° C., 42.8 g (0.38 mol) of 30% strength hydrogen peroxide were then added dropwise. After five hours of stirring at 50° C., the mixture was cooled and stirred into ice-water, and the precipitated white needles were filtered off, washed with water and dried.

Yield: 21.7 g (87.2%)

Melting point: 282° C.

Step f)

8-Methyl-2,3-dihydro-1,1,4,4-tetraoxobenz[1,4]dithiin-7-carbonyl chloride 10.0 g (0.0345 mol) of 8-methyl-2,3-dihydro-1,1,4,4-tetraoxobenz-[1,4]dithiin-7-carboxylic acid were dissolved in 100 ml of toluene, and two drops of dimethylformamide and then 4.5 g (0.038 mol) of thionyl chloride were added. After four hours of stirring under reflux, the mixture was concentrated. The colorless oil that remained (yield 10.6 g) could be directly employed further.

Step g)

1-Ethyl-5-hydroxy-4-(8-methyl-2,3-dihydro-1,1,4,4-tetraoxobenz[1,4]dithiin-7-yl)carbonylpyrazole 5.0 g (0.017 mol) of 8-methyl-2,3-dihydro-1,1,4,4-tetraoxobenz[1,4]dithiin-7-carboxylic acid were dissolved in 50 ml of acetonitrile, and 1.93 g (0.017 mol) of 1-ethyl-5-hydroxypyrazole and 3.56 g (0.017 mol) of N,N-dicyclohexylcarbodiimide were added. The reaction mixture was stirred at 20° C. for one hour and then taken up in 100 ml of 2% sodium bicarbonate solution, the precipitate that formed was filtered off with suction and the filtrate was dried and concentrated. The remaining white solid (5.8 g) was subsequently dissolved in 15 ml of dioxane, 4.2 g (0.03 mol) of potassium carbonate were added and the mixture was heated under reflux for 3 hours. After cooling, water was added, the mixture was washed with ethyl acetate, the aqueous phase was adjusted to pH 3 using 2N hydrochloric acid and the precipitate was filtered off with suction, washed with water and dried.

Yield: 2.6 g (37.8%) of colorless crystals.

$^1$H-NMR (CDCl$_3$, δ in ppm): 7.97 (d, 1H); 7.80 (d, 1H); 7.45 (s, 1H); 4.41 (s, 4H); 3.90 (q,2H); 2.59 (s, 3H); 1.26 (t, 3H).

Step h)

1-Ethyl-4-(8-methyl-2,3-dihydro-1,1,4,4-tetraoxobenz[1,4]dithiin-7-yl)carbonyl-5-propylcarbonyloxypyrazole 1.5 g (3.9 mmol) of 1-ethyl-5-hydroxy-4-(8-methyl-2,3-dihydro-1,1,4,4-tetraoxobenz[1,4]dithiin-7-yl)carbonylpyrazole were suspended in 20 ml of methylene chloride, and 0.42 g (3.9 mmol) of butyryl chloride and 0.39 g (0.42 mol) of triethylamine were added. After five hours of stirring at 20° C., the mixture was washed with 2N hydrochloric acid, sodium bicarbonate solution and water, dried and filtered off, and the solvent was distilled off. The residue was subsequently chromatographed over silica gel (mobile phase: ethyl acetate/cyclohexane=2/3).

Yield: 0.85 g (50%) of colorless crystals.

Melting point: 90° C.

In addition to the abovementioned compounds, further pyrazolyldioxothiochromanoyl derivatives of the formula I which were prepared or are preparable in a similar manner are listed in Table 2:

TABLE 2

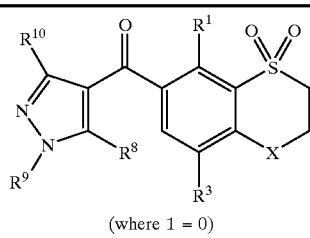

(where 1 = 0)

| No. | X | R$^1$ | R$^3$ | R$^8$ | R$^9$ | R$^{10}$ | Physical data (m.p.[° C.]; $^1$H-NMR [ppm]; MS[m/z]) |
|---|---|---|---|---|---|---|---|
| 2.1 | C(CH$_3$)$_2$ | CH$_3$ | H | Cl | CH$_2$CH$_3$ | H | 133 |
| 2.2 | C(CH$_3$)$_2$ | CH$_3$ | H | Cl | CH$_3$ | H | 138 |
| 2.3 | C(CH$_3$)$_2$ | CH$_3$ | H | OCO(CH$_2$)$_2$CH$_3$ | CH$_2$CH$_3$ | H | 124 |

TABLE 2-continued

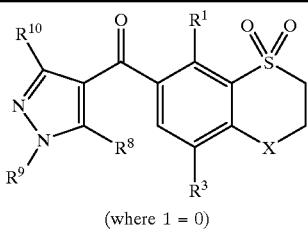

Ia (where 1 = 0)

| No. | X | $R^1$ | $R^3$ | $R^8$ | $R^9$ | $R^{10}$ | Physical data (m.p.[° C.]; $^1$H-NMR [ppm]; MS[m/z]) |
|---|---|---|---|---|---|---|---|
| 2.4 | $C(CH_3)_2$ | $CH_3$ | H | $OCH_2COC_6H_5$ | $CH_2CH_3$ | H | 158 |
| 2.5 | $SO_2$ | $CH_3$ | H | $OCO(CH_2)CH_3$ | $CH_2CH_3$ | H | 90 |
| 2.6 | $SO_2$ | $CH_3$ | H | $OCOC(CH_3)_3$ | $CH_3$ | H | 209 |
| 2.7 | $SO_2$ | $CH_3$ | H | $OCOC_6H_5$ | $CH_3$ | H | 240 |
| 2.8 | $SO_2$ | $CH_3$ | H | $OCOCH_3$ | $CH_3$ | H | 180 (decomposition) |
| 2.9 | $SO_2$ | $CH_3$ | H | $OCOCH(CH_3)_2$ | $CH_3$ | H | 187 (decomposition) |
| 2.10 | $SO_2$ | $CH_3$ | H | OCO(2-furyl) | $CH_3$ | H | 227 |
| 2.11 | $SO_2$ | $CH_3$ | H | OCO(2-thienyl) | $CH_3$ | H | 237 |
| 2.12 | $SO_2$ | $CH_3$ | H | OCO[2-Cl-5-(1'-CH$_3$-6'-CF$_3$-2',4'-dioxo-(1'H,3'H)-pyrimidinyl-3'-yl)-C$_6$H$_3$] | $CH_3$ | $CH_3$ | 186 |
| 2.13 | $SO_2$ | $CH_3$ | H | $OCO(CH_2)_8CO_2CH_2CH_3$ | $CH_2CH_3$ | H | oil; 596 (m/z) |
| 2.14 | $SO_2$ | $CH_3$ | H | $OCOCH_2$(2-norbornyl) | $CH_2CH_3$ | H | 111 |
| 2.15 | $SO_2$ | $CH_3$ | H | OCO[4-(2'-Cl-4'-CF$_3$—C$_6$H$_3$)—O-2-NO$_2$—C$_6$H$_3$] | $CH_2CH_3$ | H | 116 |
| 2.16 | $SO_2$ | $CH_3$ | H | OCO[3,7-Cl$_2$-quinolin-8-yl] | $CH_2CH_3$ | H | 117 |
| 2.17 | $SO_2$ | $CH_3$ | H | OCO[2,5-Cl$_2$-6-OCH$_3$—C$_6$H$_2$] | $CH_2CH_3$ | H | 160 |
| 2.18 | $SO_2$ | $CH_3$ | H | $OCO(CH_2)_8CH=CH_2$ | $CH_2CH_3$ | H | oil; 550 (m/z) |

The compounds of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca,* Glycine max, *Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Suitable as inert auxiliaries are essentially the following:

mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the pyrazolyldioxothiochromanoyl derivatives of the formula I, either as such or dissolved in an oil or solvent, can be homogenized in water by means of a wetting agent, tackifier, dispersant or emulsifier. Alternatively, it is also possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for scattering and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

The formulation examples below illustrate the preparation of such compositions:

I. 20 parts by weight of the compound No. 2.4 are dissolved in a mixture composed of 80 parts by weight of alkylated benzene, 10 parts by weight of the adduct of from 8 to 10 mol of ethylene oxide to 1 mol of oleic acid N-monoethanol-amide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. 2.5 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the compound No. 2.6 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the compound No. 2.8 are mixed thoroughly with 3 parts by weight of sodium diisobutyl-naphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the compound No. 2.10 are mixed with 97 parts by weight of finely divided kaolin. This gives a dust which comprises 3% by weight of the active ingredient.

VI. 20 parts by weight of the compound No. 2.9 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 2.11 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 2.12 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

The rates of application of the compound of the formula I are from 0.001 to 3.0, preferably 0.01 to 1.0, kg/ha of active substance (a.s.), depending on the control target, the season, the target plants and the growth stage.

To widen the spectrum of action and to achieve synergistic effects, the pyrazolyldioxothiochromanoyl derivatives of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het) aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

Use Examples

The herbicidal activity of the pyrazolyldioxothiochromanoyl derivatives of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this was adversely affected by the active ingredients. The rate of application for the pre-emergence treatment was 0.25 or 0.125 kg/ha of a.s.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The rate of application for the post-emergence treatment was 0.125 or 0.0625 kg/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
|---|---|
| Chenopodium album | lambsquarters (goosefoot) |
| Echinochloa crus-galli | barnyardgrass |
| Galium aparine | catchweed bedstraw |
| Ipomoea spp. | morningglory |
| polygonum persicaria | ladysthumb |
| Setaria faberi | giant foxtail |
| Setaria viridis | green foxtail |
| Sinapis alba | white mustard |
| Solanum nigrum | black nightshade |
| Zea mays | corn |

At application rates of 0.125 or 0.0625 kg/ha, the compound 2.8, applied post-emergence, showed very good action against the undesirable plants lambsquarters, ladysthumb, giant foxtail, green foxtail and white mustard. Likewise, the compound 2.12 showed, at the abovementioned application rates, applied post-emergence, very good action against lambsquarters, barnyardgrass, catchweed bedstraw, morningglory and black nightshade. Furthermore, the compound 2.5, applied pre-emergence at application rates of 0.25 or 0.125 kg/ha, controlled undesirable grasses such as barnyardgrass and giant foxtail very well, and was at the same time compatible with corn.

We claim:

1. A pyrazolyldioxothiochromanoyl derivative of the formula I

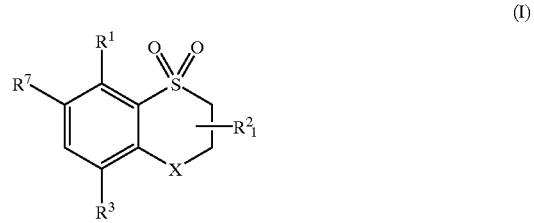

(I)

where:

X is oxygen, sulfur, S=O, S(=O)$_2$, CR$^4$R$^5$, C=O or C=NR$^6$;

R$^1$ is hydrogen, nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, aminosulfonyl, N-(C$_1$–C$_6$-alkyl)aminosulfonyl, N,N-di (C$_1$–C$_6$-alkyl)aminosulfonyl, N-(C$_1$–C$_6$-alkylsulfonyl) amino, N-(C$_1$–C$_6$-haloalkylsulfonyl)amino, N-(C$_1$–C$_6$-alkyl)-N-(C$_1$–C$_6$-alkylsulfonyl)amino or N-(C$_1$–C$_6$-alkyl)-N-(C$_1$–C$_6$-haloalkylsulfonyl)amino;

R$^2$ is C$_1$–C$_6$-alkyl, C$_1$–C$_6$-haloalkyl, C$_1$–C$_6$-alkoxy or C$_1$–C$_6$-haloalkoxy;

R$^3$ is hydrogen, C$_1$–C$_6$-alkyl or halogen;

R$^4$,R$^5$ are hydrogen, nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, N-C$_1$–C$_6$-alkylamino, N-C$_1$–C$_6$-haloalkylamino, N,N-di(C$_1$–C$_6$- alkyl)amino, N-$C_1$-$C_6$-alkoxyamino, N-($C_1$-$C_6$-alkoxy)-N-($C_1$-$C_6$-alkyl)amino, 1-tetrahydropyrrolyl, 1-piperidinyl, 4-morpholinyl or 1-hexahydropyrazinyl; or $R^4$ and $R^5$ together form an —O—$(CH_2)_m$—O—, —O—$(CH_2)_m$—S—, —S—$(CH_2)_m$—S— or —O—$(CH_2)_n$— chain which may be substituted by one to three radicals selected from the following group: halogen, cyano, $C_1$–$C_4$-alkyl, $C_1$–$C_4$-haloalkyl or $C_1$–$C_4$-alkoxycarbonyl; or $R^4$ and $R^5$ together form a —$(CH_2)_p$— chain which may be interrupted by oxygen or sulfur and/or may be substituted by one to four radicals selected from the following group: halogen, cyano, $C_1$–$C_4$-alkyl, $C_1$–$C_4$-haloalkyl or $C_1$–$C_4$-alkoxycarbonyl; or $R^4$ and $R^5$ together form a methylidene group which may be substituted by one or two radicals selected from the following group: halogen, cyano, hydroxyl, formyl, $C_1$–$C_6$-alkyl, $C_1$–$C_6$-haloalkyl, $C_1$–$C_6$-alkoxy, $C_1$–$C_6$-haloalkoxy, $C_1$–$C_6$alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^6$ is $C_1$–$C_6$-alkyl, $C_1$–$C_6$-haloalkyl, $C_1$–$C_6$-alkoxy or $C_1$–$C_6$-haloalkoxy;

l is 0 to 4;
m is 2 to 4;
n is 1 to 5;
p is 2 to 5;
$R^7$ is a compound IIa or IIb

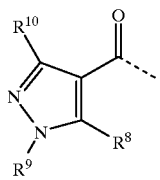

IIa

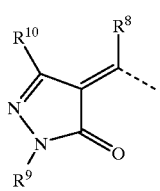

IIb where $R^8$ is halogen, $OR^{11}$, $SR^{11}$, $SOR^{12}$, $SO_2R^{12}$, $POR^{12}R^{13}$, $OPOR^{12}R^{13}$, $OPSR^{12}R^{13}$, $NR^{14}R^{15}$, $ONR^{15}R^{15}$, N-bonded heterocyclyl or O-(N-bonded heterocyclyl), where the heterocyclyl radical of the two lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^9$ is hydrogen, $C_1$–$C_6$-alkyl, $C_1$–$C_6$-haloalkyl, hydroxyl, $C_1$–$C_6$-alkoxy or $C_1$–$C_6$-haloalkoxy;

$R^{10}$ is hydrogen, halogen, $C_1$–$C_6$-alkyl, $C_1$–$C_6$-haloalkyl, hydroxyl, $C_1$–$C_6$-alkoxy, $C_1$–$C_6$-haloalkoxy, $C_1$–$C_6$-alkylthio or $C_1$–$C_6$-haloalkylthio;

$R^{11}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_{20}$-alkylcarbonyl, $C_2$–$C_{20}$-alkenylcarbonyl, $C_2$–$C_6$-alkynylcarbonyl, $C_3$–$C_6$-cycloalkylcarbonyl, (2-norbornyl)methylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$alkynyl)-N-($C_1$–$C_6$-alkyl)aminocarbonyl, N-($C_1$–$C_6$-alkoxy)-N-($C_1$–$C_6$-alkyl)aminocarbonyl, N-($C_3$–$C_6$alkenyl )-N-($C_1$–$C_6$-alkoxy)aminocarbonyl, N-($C_3$–$C_6$-alkynyl)-N-($C_1$–$C_6$-alkoxy)aminocarbonyl, di($C_1$–$C_6$alkyl) aminothiocarbonyl, $C_1$–$C_6$-alkylcarbonyl-$C_1$–$C_6$-alkyl, $C_1$–$C_6$-alkoxyamino-$C_1$–$C_6$-alkyl, N-($C_1$–$C_6$-alkylamino)imino-$C_1$–$C_6$-alkyl or N,N-di($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, di($C_1$–$C_4$-alkyl) amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenylaminocarbonyl, N-($C_1$–$C_6$-alkyl)-N-(phenyl)aminocarbonyl, heterocyclylaminocarbonyl, N-($C_1$–$C_6$-alkyl)-N-(heterocyclyl)aminocarbonyl, phenyl-$C_2$–$C_6$-alkenylcarbonyl or heterocyclyl-$C_2$–$C_6$-alkenylcarbonyl, where the phenyl and the heterocyclyl radical of the 18 lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy, phenoxy, heterocyclyl or N-bonded heterocyclyl, where the three lastmentioned substituents for their part may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{12}$, $R^{13}$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, amino, $C_1$–$C_6$-alkylamino, $C_1$–$C_6$-haloalkylamino, di($C_1$–$C_6$-alkyl)amino or di($C_1$–$C_6$-haloalkyl)amino, where the abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

are phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three radicals of the following group: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylamino-carbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{15}$ is $C_1$–$C_6$-alkyl, $C_3$–$C_6$-alkenyl, $C_3$–$C_6$-alkynyl or $C_1$–$C_6$-alkylcarbonyl;

and agriculturally useful salts thereof.

2. A process for preparing compounds of the formula I as claimed in claim 1 where $R^8$=halogen, which comprises reacting a pyrazolone derivative of the formula III,

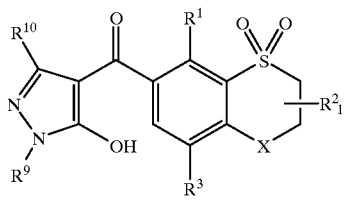

(III)

where the variables $R^1$ to $R^{10}$, X, l are as defined in claim 1 with a halogenating agent.

3. A process for preparing compounds of the formula I as claimed in claim 1 where $R^8$=$OR^{11}$, $OPOR^{12}R^{13}$ or $OPSR^{12}R^{13}$, which comprises reacting a pyrazolone derivative of the formula III,

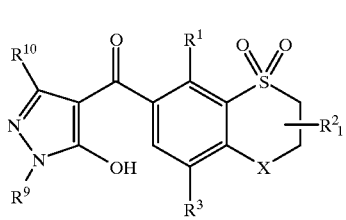

(III)

where the variables $R^1$ to $R^{10}$, X, l are as defined in claim 1 with a compound of the formula IVα, IVβ or IVγ,

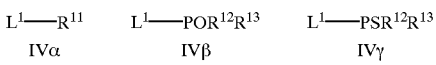

where the variables $R^{11}$ to $R^{13}$ are as defined in claim 1 and $L^1$ is a nucleophilically replaceable leaving group.

4. A process for preparing compounds of the formula I as claimed in claim 1 where $R^8$=$OR^{11}$, $SR^{11}$, $POR^{12}R^{13}$, $NR^{14}R^{15}$, $ONR^{15}R^{15}$, N-bonded heterocyclyl or O—N-bonded heterocyclyl, which comprises reacting a compound of the formula

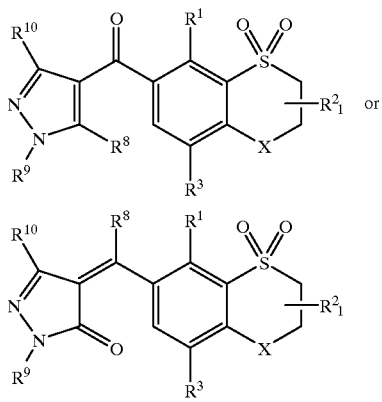

where $R^8$ is halogen and the variables $R^1$ to $R^3$, $R^9$ and $R^{10}$, X and l are as defined in claim 1 with a compound of the formula Vα, Vβ, Vγ, Vδ, Vε, Vη or Vθ,

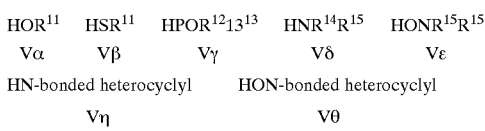

where the variables $R^{11}$ to $R^{15}$ are as defined in claim 1, optionally in the presence of a base.

5. A process for preparing compounds of the formula I as claimed in claim 1 where $R^8$=$SOR^{12}$, $SO_2R^{12}$, which comprises reacting a compound of the formula

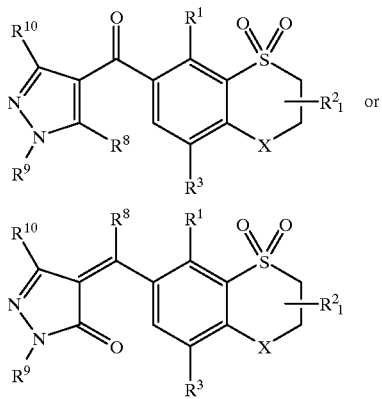

where $R^8$ is $SR^{12}$ and the variables $R^1$ to $R^3$, $R^9$, $R^{10}$, $R^{12}$, X and l are as defined in claim 1 with an oxidizing agent.

6. A process for preparing compounds of the formula I where $R^7$=IIa as claimed in claim 1, wherein a metallated pyrazole derivative of the formula VI where M is a metal and $R^8$ to $R^{10}$ are each as defined in claim 1 is reacted with a dioxothiochromancarboxylic acid derivative of the formula VII where $R^1$ to $R^3$, X and l are each as defined in claim 1 and $L^2$ is a nucleophilically replaceable leaving group.

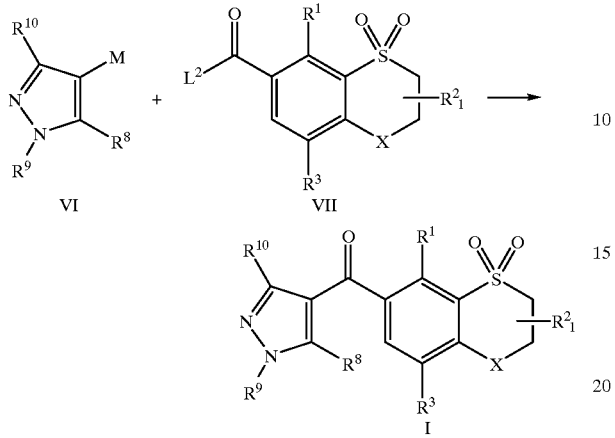

7. A composition, comprising a herbicidally effective amount of at least one pyrazolyldioxothiochromanoyl derivative of the formula I or an agriculturally useful salt of I as claimed in claim 1, and auxiliaries which are customary for the formulation of crop protection agents.

8. A process for preparing a composition as claimed in claim 7, which comprises mixing a herbicidally effective amount of at least one pyrazolyldioxothiochromanoyl derivative of the formula I or an agriculturally useful salt of I and auxiliaries which are customary for the formulation of crop protection agents.

9. A method for controlling undesirable vegetation, which comprises allowing a herbicidally effective amount of at least one pyrazolyldioxothiochromanoyl derivative of the formula I or an agriculturally useful salt of I as claimed in claim 1 to act on plants, their habitat and/or on seeds.

10. A pyrazolyldioxothiochromanoyl derivative of the formula I as defined in claim 1, wherein
X is $S(=O)_2$ or $CR^4R^5$.

11. A pyrazolyldioxothiochromanoyl derivative of the formula I as defined in claim 1, wherein
$R^1$ is halogen, $C_1$–$C_6$-alkyl, $C_1$–$C_6$-haloalkyl, $C_1$–$C_6$-alkoxy, $C_1$–$C_6$-alkylthio or $C_1$–$C_6$- alkylsulfonyl.

12. A pyrazolyldioxothiochromanoyl derivative of the formula I as defined in claim 1, wherein
$R^1$ is halogen, $C_1$–$C_6$-alkyl or $C_1$–$C_6$-alkoxy.

13. A pyrazolyldioxothiochromanoyl derivative of the formula I as defined in claim 1, wherein
$R^3$ is hydrogen.

14. A pyrzolyldioxothiochromanoyl derivative of the formula I as defined in claim 1, wherein
$R^4$ is hydrogen, $C_1$–$C_6$-alkyl, $C_1$–$C_6$-haloalkyl, $C_1$–$C_6$-alkoxy, or $C_1$–$C_6$-haloalkoxy;
$R^5$ is hydrogen or $C_1$–$C_6$-alkyl.

15. A pyrazolyldioxothiochromanoyl derivative of the formula I as defined in claim 1, wherein
l is O.

16. A pyrazolyldioxothiochromanoyl derivative of the formula I as defined in claim 1, wherein
$R^8$ is $NR^{14}R^{15}$ or N-bonded heterocyclyl which may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy.

17. A pyrazolyldioxothiochromanoyl derivative of the formula I as defined in claim 1, wherein $R^8$ is $OR^{11}$.

18. A pyrazolydioxothiochromanoyl derivative of the formula I as defined in claim 1, wherein
$R^{11}$ is $C_1$–$C_{20}$-alkylcarbonyl, $C_1$–$C_{20}$-alkenylcarbonyl, $C_2$–$C_6$-alkynylcarbonyl, $C_3$–$C_8$- cycloalkylcarbonyl or (2-norbonyl)methylcarbonyl, where the abovementioned alkyl and cycloalkyl radicals may be partially or fully halogenated and/or may carry one to three of the following groups:
cyano, $C_1$–$C_4$-alkoxy, $C_1$–$C_4$-alkythio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl) amino- $C_1$–$C_4$-alkoxycarbonyl, hydroxycarbonyl, $C_1$–$C_4$-alkylaminocarbonyl, di-($C_1$–$C_4$- alkyl) aminocarbonyl, aminocarbonyl, $C_{1-4}$-alkylcarbonyloxy or $C_3$–$C_6$-cycloalkyl; is phenylcarbonyl-$C_1$–$C_6$-alkyl, heterocyclylcarbonyl-$C_1$–$C_6$-alkyl, phenylcarbonyl or heterocyclylcarbonyl, where the phenyl and the heterocyclyl radical of the four last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy, $C_1$–$C_4$-haloalkoxy, phenoxy, heterocyclyl or N-bonded heterocylcyl where the three last-mentioned substituents for their part may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy.

19. A pyrazolyldioxothiochromanoyl derivative of the formula I as defined in claim 1, wherein
X is $S(=O)_2$ $CR^4R^5$;
$R^1$ is halogen or $C_1$–$C_6$-alkyl;
$R^3$ is hydrogen;
$R^4$ is hydrogen or $C_1$–$C_6$-alkyl;
$R^5$ is hydrogen or $C_1$–$C_6$-alkyl;
l is 0;
$R^7$ is compound Ia;
$R^8$ is halogen or $OR^{11}$;
$R^9$ is $C_1$–$C_6$-alkyl;
$R^{10}$ is hydrogen or $C_1$–$C_6$-alkyl;
$R^{11}$ is $C_1$–$C_{20}$-alkenylcarbonyl, or (2-norbornyl)methylcarbonyl, where the alkyl radical may b partially or fully halogenated and/or may carry one to three of the following groups:
cyano, $C_1$–$C_4$-alkoxy, $C_1$–$C_4$-alkythio, di-($C_1$–$C_4$-alkyl)amino, $C_1$–$C_4$-alkylcarbonyl, $C_1$–$C_4$-alkoxycarbonyl, hydroxycarbonyl, $C_1$–$C_4$-alkylaminocarbonyl, di-($C_1$–$C_4$- alkyl) aminocarbonyl, aminocarbonyl or $C_3$–$C_6$-cycloalkyl;
is phenylcarbonyl-$C_1$–$C_6$-alkyl, phenylcarbonyl or heterocarbonyl, where the phenyl and the heterocyclyl radical of the three last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy, phenoxy, heterocyclyl or N-bonded heterocyclyl where the three last-mentioned substituents for their part may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy.

* * * * *

UNITED STATES PATENT AND TRADEMARK OFFICE
CERTIFICATE OF CORRECTION

PATENT NO. : 6,326,333 B1  Page 1 of 1
DATED : December 4, 2001
INVENTOR(S) : Witschel et al.

It is certified that error appears in the above-identified patent and that said Letters Patent is hereby corrected as shown below:

Column 72,
Line 5, "$C_3$-$C_8$" should be -- $C_3$-$C_6$ --.
Line 45, "may b partially" should be -- may be partially --.

Signed and Sealed this

Fourth Day of June, 2002

Attest:

Attesting Officer

JAMES E. ROGAN
Director of the United States Patent and Trademark Office